United States Patent
Ouyang et al.

(10) Patent No.: US 11,081,230 B2
(45) Date of Patent: Aug. 3, 2021

(54) SYSTEMS AND METHODS FOR IMAGE PROCESSING

(71) Applicant: SHANGHAI UNITED IMAGING HEALTHCARE CO., LTD., Shanghai (CN)

(72) Inventors: Bin Ouyang, Shanghai (CN); Qingzhen Ma, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 42 days.

(21) Appl. No.: 16/133,652

(22) Filed: Sep. 17, 2018

(65) Prior Publication Data
US 2019/0088361 A1     Mar. 21, 2019

(30) Foreign Application Priority Data
Sep. 18, 2017   (CN) .......................... 201710841203.7

(51) Int. Cl.
*A61B 5/00*     (2006.01)
*G06T 3/40*     (2006.01)
(Continued)

(52) U.S. Cl.
CPC .......... *G16H 30/40* (2018.01); *A61B 5/0013* (2013.01); *A61B 5/7425* (2013.01); (Continued)

(58) Field of Classification Search
CPC ..... A61B 5/0013; A61B 5/055; A61B 5/7425; A61B 5/7435; G06T 2207/20221; (Continued)

(56) References Cited

U.S. PATENT DOCUMENTS

| 2002/0140829 A1* | 10/2002 | Colavin | G06T 3/403 |
| | | | 348/231.99 |
| 2007/0263233 A1* | 11/2007 | Mei | H04N 1/3877 |
| | | | 358/1.2 |

(Continued)

FOREIGN PATENT DOCUMENTS

| CN | 101196962 A | 6/2008 |
| CN | 101764885 A | 6/2010 |

(Continued)

OTHER PUBLICATIONS

First Office Action in Chinese Application No. 201710841203.7 dated Jun. 18, 2020, 19 pages.
(Continued)

*Primary Examiner* — David Bilodeau
(74) *Attorney, Agent, or Firm* — Metis IP LLC

(57) ABSTRACT

A method for stitching image for medical imaging device may include obtaining a plurality of image series. Each of the plurality of image series may include one or more scanning images. The method may also include, for each of the plurality of image series, determining a tag of the each of the plurality of image series and classifying the plurality of image series based on the tags of the plurality of image series. The method may further include determining one or more groups of image series based on the classification. Image series in a same group may have a same tag. The method may also include stitching at least one image series of at least one group of the one or more groups of image series.

19 Claims, 18 Drawing Sheets

(51) Int. Cl.
*A61B 5/055* (2006.01)
*G16H 30/40* (2018.01)
*G06T 5/50* (2006.01)
*G16H 30/20* (2018.01)

(52) U.S. Cl.
CPC .......... *A61B 5/7435* (2013.01); *G06T 3/4038* (2013.01); *G06T 5/50* (2013.01); *G16H 30/20* (2018.01); *A61B 5/055* (2013.01); *G06T 2207/20221* (2013.01)

(58) Field of Classification Search
CPC ......... G06T 3/4038; G06T 5/50; G16H 30/20; G16H 30/40
See application file for complete search history.

(56) References Cited

U.S. PATENT DOCUMENTS

| | | |
|---|---|---|
| 2012/0092268 A1 | 4/2012 | Tsai et al. |
| 2012/0195523 A1* | 8/2012 | Fu .......................... H04N 1/387 382/294 |
| 2012/0200665 A1* | 8/2012 | Furumura ............. G06T 3/0062 348/36 |
| 2012/0306784 A1 | 12/2012 | Axelsson |
| 2013/0121525 A1* | 5/2013 | Chen ..................... G06T 3/0062 382/100 |
| 2014/0258905 A1 | 9/2014 | Lee et al. |
| 2014/0267588 A1* | 9/2014 | Areas .................... G06T 3/4038 348/36 |
| 2015/0117769 A1 | 4/2015 | Mayer et al. |
| 2015/0199121 A1 | 7/2015 | Gulaka et al. |
| 2016/0203354 A1* | 7/2016 | Choi .................. G06K 9/00026 382/124 |
| 2016/0274750 A1 | 9/2016 | Stewart |
| 2017/0006219 A1* | 1/2017 | Adsumilli .............. H04N 5/247 |
| 2017/0256040 A1* | 9/2017 | Grauer ............... H04N 1/00196 |
| 2018/0262683 A1* | 9/2018 | Meler ....................... G06T 7/70 |
| 2018/0330471 A1* | 11/2018 | Qin ............................ G06T 5/50 |

FOREIGN PATENT DOCUMENTS

| | | |
|---|---|---|
| CN | 101782927 A | 7/2010 |
| CN | 103425395 A | 12/2013 |
| CN | 103544687 A | 1/2014 |
| CN | 105095910 A | 11/2015 |
| CN | 106502498 A | 3/2017 |
| CN | 106681599 A | 5/2017 |
| CN | 106951152 A | 7/2017 |

OTHER PUBLICATIONS

First Office Action in Chinese Application No. 201710859020.8 dated Apr. 14, 2020, 17 pages.

* cited by examiner

SYSTEMS AND METHODS FOR IMAGE PROCESSING

CROSS-REFERENCE TO RELATED APPLICATIONS

This application claims priority to Chinese Patent Application No. 201710841203.7 filed on Sep. 18, 2017, the entire contents of which are hereby incorporated by reference.

TECHNICAL FIELD

The present disclosure generally relates to systems and methods for image processing, and more specifically, systems and methods for stitching images.

BACKGROUND

Due to the limitations of medical imaging technology, a single image series, obtained based on a scan, may not include all interested parts of a subject, such as a human body. It may be then desirable to generate an image that includes more information than one single image series according to multiple image series acquired based on multiple scans. Additionally, imaging methods may be employed to scan a subject, which may produce various types of image series different from each other. Therefore, it may be further desirable to develop systems and methods for combining multiple image series with various types into larger images in order to present the user more comprehensive imaging information in one place.

SUMMARY

According to an aspect of the present disclosure, a method for image processing may be provided. The method may include one or more of the following operations. A processor may obtain a plurality of image series. Each of the plurality of image series may include one or more scanning images. For each of the plurality of image series, the processor may determine a tag of the each of the plurality of image series. The processor may classify the plurality of image series based on the tags of the plurality of image series. The processor may determine one or more groups of image series based on the classification, image series in a same group having a same tag. Furthermore, the processor may stitch at least one image series of at least one group of the one or more groups of image series.

In some embodiments, the processor display, by a display, a plurality of stitching algorithms. The processor may receive, by an input device, one or more instructions from a user. The processor may determine a selected stitching algorithm among the plurality of stitching algorithms based on the one or more instructions. The processor may stitch the at least one image series of the at least one group of the one or more groups of image series according to the selected stitching algorithm.

In some embodiments, the processor may stitch all image series of the at least one group of the one or more groups of image series.

In some embodiments, the processor may receive, by an input device, a first selection instruction. The processor may select at least one image series of at least one group of the one or more groups of image series according to the first selection instruction. The processor may stitch the selected at least one image series.

In some embodiments, the processor may determine the number of image series for each of the at least one group of the one or more groups of image series. The processor may determine a plurality of stitching combinations based on the number of image series corresponding to each of the at least one of the one or more groups of image series. The processor may stitch at least one of the plurality of stitching combinations.

In some embodiments, the processor may display a stitching result by a display.

In some embodiments, the processor may receive, by an input device, a second selection instruction. The processor may select one or more specific groups among the one or more groups of image series based on the second selection instruction. The processor may stitch the at least one image series of one group for each of the one or more specific groups of image series.

In some embodiments, the processor, for each of the image series in a group, determine a sub-tag for the each of the image series of the group. The processor may classify the image series in the group based on the sub-tags of the image series. In some embodiments, the processor may determine one or more sub-groups of the image series in the group according to the classification based on the sub-tags of the image series, image series in a same sub-group having a same sub-tag. In some embodiments, the processor may stitch at least one image series of at least one sub-group of the one or more sub-groups of image series.

In some embodiments, the tag may include at least one of a protocol title, a specific mark, or a name format of the plurality of image series.

According to another aspect of the present disclosure, a system is provided. The system may include at least one non-transitory computer-readable storage medium and at least one processor. The at least one storage medium may include a set of instructions. The at least one processor may be in communication with the at least one non-transitory computer-readable storage medium. When executing the instructions, the at least one processor may be configured to cause the system to perform one or more of the following operations. The at least one processor may obtain a plurality of image series. Each of the plurality of image series may include one or more scanning images. For each of the plurality of image series, the at least one processor may determine a tag of the each of the plurality of image series. The at least one processor may classify the plurality of image series based on the tags of the plurality of image series. The at least one processor may determine one or more groups of image series based on the classification, image series in a same group having a substantially same tag. Furthermore, the at least one processor may stitch at least one image series of at least one group of the one or more groups of image series.

In some embodiments, the at least one processor may be further configured to cause the system to: display a plurality of stitching algorithms; receive one or more instructions from a user, and determine a selected stitching algorithm among the plurality of stitching algorithms based on the one or more instructions. To stitch the at least one image series of the at least one group of the one or more groups of image series, the at least one processor may be further configured to cause the system to stitch the at least one image series of the at least one group of the one or more groups of image series according to the selected stitching algorithm.

In some embodiments, to stitch the at least one image series of at least one group of the one or more groups of image series, the at least one processor may be configured to cause the system to stitch all image series of the at least one group of the one or more groups of image series.

In some embodiments, to stitch the at least one image series of at least one group of the one or more groups of image series, the at least one processor may be configured to cause the system to: receive a first selection instruction; select at least one image series of at least one group of the one or more groups of image series according to the first selection instruction; and stitch the selected at least one image series.

In some embodiments, to stitch the at least one image series of at least one group of the one or more groups of image series, the at least one processor may be configured to cause the system to: determine the number of image series for each of the at least one group of the one or more groups of image series; determine a plurality of stitching combinations based on the number of image series corresponding to each of the at least one of the one or more groups of image series; and stitch least one of the plurality of stitching combinations.

In some embodiments, the image series in a same group may have a same sub-tag.

In some embodiments, the at least one processor may be further configured to cause the system to display a stitching result by a display.

In some embodiments, to stitch the at least one image series of at least one group of the one or more groups of image series, the at least one processor may be configured to cause the system to: receive a second selection instruction; select one or more specific groups among the one or more groups of image series based on the second selection instruction; and stitch the at least one image series of one group for each of the one or more specific groups of image series by the at least one processor.

In some embodiments, the at least one processor may be further configured to cause the system to: for each of the image series in a group, determine a sub-tag for the each of the image series of the group; classify the image series in the group based on the sub-tags of the image series; determine one or more sub-groups of the image series in the group according to the classification based on the sub-tags of the image series, image series in a same sub-group having a substantially same sub-tag; and stitch at least one image series of at least one sub-group of the one or more sub-groups of image series.

In some embodiments, the tag may include at least one of a protocol title, a specific mark, or a name format of the plurality of image series.

According to another aspect of the present disclosure, a non-transitory computer-readable medium embodying a computer program product is provided. The computer program product may comprise instructions that cause a computing device to effectuate a method. The method may include one or more of the following operations. The computing device may obtain a plurality of image series. Each of the plurality of image series may include one or more scanning images. For each of the plurality of image series, the computing device may determine a tag of the each of the plurality of image series. The computing device may classify the plurality of image series based on the tags of the plurality of image series. The computing device may determine one or more groups of image series based on the classification, image series in a same group having a substantially same tag. Furthermore, the computing device may stitch at least one image series of at least one group of the one or more groups of image series.

BRIEF DESCRIPTION OF THE DRAWINGS

The present disclosure is further described in terms of exemplary embodiments. These exemplary embodiments are described in detail with reference to the drawings. These embodiments are non-limiting examples, in which like reference numerals represent similar structures throughout the several views of the drawings, and wherein.

DETAILED DESCRIPTION

Figure 1:
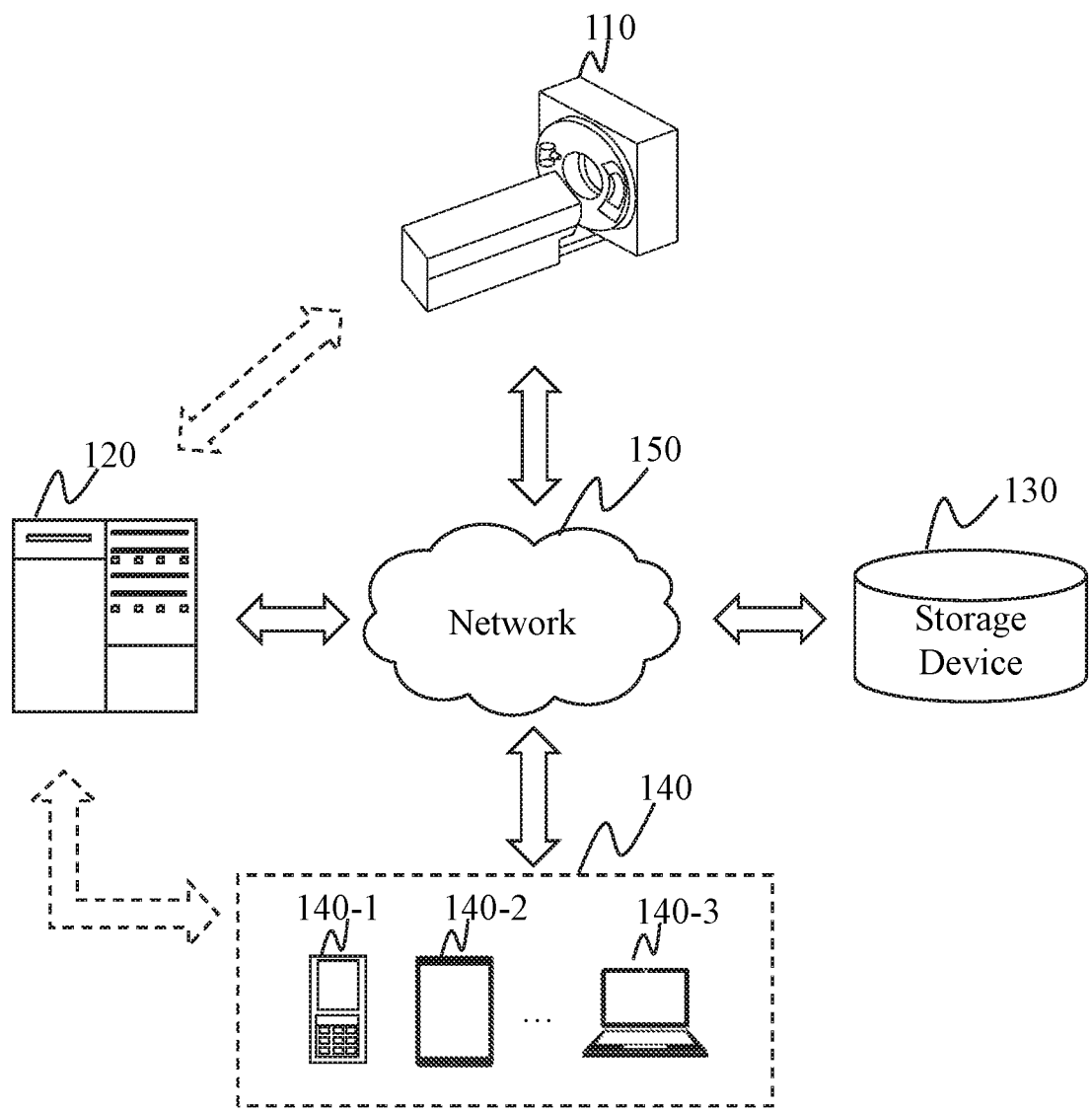
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by another expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The following description is provided to help better understanding an image processing methods and/or systems. The methods and/or systems may be applied for the non-invasive imaging, such as for disease diagnosis or research purposes. The term "image" used in this disclosure may refer to a 2D image, a 3D image, a 4D image, and/or any related image data (e.g., CT data, projection data corresponding to the CT data). This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

An aspect of this present disclosure relates to a system and a method for image processing, and more particularly, for image stitching. The system may obtain a plurality of image series. The plurality of image series may be generated based on scan data from a scanner. Each of image series may include one or more scanning images. The system may determine a tag of each of the plurality of image series. The system may also classify the image series having the same or substantially same tag into one group. The system may further determine one or more groups based on the classification and stitch at least one image series of at least one group of the one or more groups of image series.

FIG. 1 is a schematic diagram illustrating an exemplary imaging system 100 according to some embodiments of the present disclosure. As shown in the figure, the imaging system 100 may include a scanner 110, a processing device 120, a storage device 130, one or more terminals 140, and a network 150. The components in the imaging system 100 may be connected in various ways. Merely by way of example, as illustrated in FIG. 1, the scanner 110 may be connected to the processing device 120 through the network 150. As another example, the scanner 110 may be connected to the processing device 120 directly as indicated by the bi-directional arrow in dotted lines linking the scanner 110 and the processing device 120. As a further example, the storage device 130 may be connected to the processing device 120 through the network 150. As still a further example, one or more terminals 140 may be connected to the processing device 120 directly (as indicated by the bi-directional arrow in dotted lines linking the terminal 140 and the processing device 120) or through the network 150.

The scanner 110 may generate or provide image data via scanning a subject or a part of the subject. In some embodiments, the scanner 110 may be a medical imaging device, for example, a positron emission tomography (PET) device, a single-photon emission computed tomography (SPECT) device, a computed tomography (CT) device, a magnetic resonance imaging (MRI) device, or the like, or any combination thereof (e.g., a PET-CT device, a PET-MRI device, etc.). In some embodiments, the scanner 110 may include a single-modality scanner. The single-modality scanner may include, for example, a magnetic resonance imaging (MRI) scanner, a computed tomography (CT) scanner, and/or a positron emission tomography (PET) scanner. In some embodiments, the scanner 110 may include both the CT scanner and the PET scanner. In some embodiments, image data of different modalities related to the subject, such as CT image data and PET image data, may be acquired using different scanners separately. In some embodiments, the scanner 110 may include a multi-modality scanner. The multi-modality scanner may include a positron emission tomography-computed tomography (PET-CT) scanner, a positron emission tomography-magnetic resonance imaging (PET-MRI) scanner, or the like, or any combination thereof. The multi-modality scanner may perform multi-modality imaging simultaneously. For example, the PET-CT scanner may generate structural X-ray CT image data and functional PET image data simultaneously in a single scan. The PET-MRI scanner may generate MRI data and PET data simultaneously in a single scan.

In some embodiments, the subject to be scanned may be a human body or a portion thereof, a physical object (e.g., a phantom), a substance, or the like, or any combination thereof. In some embodiments, the subject may include a specific portion of a human body, such as a head, a thorax, an abdomen, or the like, or any combination thereof. In some embodiments, the subject may include a specific organ, such as an esophagus, a trachea, a bronchus, a stomach, a gallbladder, a small intestine, a colon, a bladder, a ureter, a uterus, a fallopian tube, etc. In some embodiments, the subject may include a physical model (also referred to as a mockup). The physical model may include one or more materials constructed as different shapes and/or dimensions. Different parts of the physical model may be made of different materials. Different materials may have different X-ray attenuation coefficients, different tracer isotopes, and/or different hydrogen proton contents. Therefore, different parts of the physical model may be recognized by the imaging system 100. In the present disclosure, "object" and "subject" are used interchangeably. In some embodiments, the scanner 110 may include a scanning table. The subject may be placed on the scanning table for imaging.

In some embodiments, the scanner 110 may transmit the image data via the network 150 to the processing device 120, the storage device 130, and/or the terminal(s) 140. For example, the image data may be sent to the processing device 120 for further processing or may be stored in the storage device 130.

The processing device 120 may process data and/or information obtained from the scanner 110, the storage device 130, and/or the terminal(s) 140. For example, the processing device 120 may obtain the scan data from the scanner 110 and generate the plurality of image series according to the scan data. The processing device 120 may stitch at least one image series into a single image. In some embodiments, the processing device 120 may be a single server or a server group. The server group may be centralized or distributed. In some embodiments, the processing device 120 may be local or remote. For example, the processing device 120 may access information and/or data from the scanner 110, the storage device 130, and/or the terminal(s) 140 via the network 150. As another example, the processing device 120 may be directly connected to the scanner 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 200 having one or more components as described in connection with FIG. 2.

The storage device 130 may store data, instructions, and/or any other information. In some embodiments, the storage device 130 may store data obtained from the scanner 110, the processing device 120, and/or the terminal(s) 140. In some embodiments, the storage device 130 may store data and/or instructions that the processing device 120 may execute or use to perform exemplary processes and methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing device 120, the terminal(s) 140, etc.). One or more components in the imaging system 100 may access the data or instructions stored in the storage device 130 via the network 150. In some embodiments, the storage device 130 may be part of the processing device 120.

The terminal(s) 140 may be connected to and/or communicate with the scanner 110, the processing device 120, and/or the storage device 130. For example, the terminal(s) 140 may obtain a processed image from the processing device 120. As another example, the terminal(s) 140 may obtain image data acquired by the scanner 110 and transmit the image data to the processing device 120 to be processed. In some embodiments, the terminal(s) 140 may include a mobile device 140-1, a tablet computer 140-2, a laptop computer 140-3, or the like, or any combination thereof. For example, the mobile device 140-1 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate the exchange of information and/or data for the imaging system 100. In some embodiments, one or more components of the imaging system 100 (e.g., the scanner 110, the processing device 120, the storage device 130, the terminal(s) 140, etc.) may communicate information and/or data with one or more other components of the imaging system 100 via the network 150. For example, the processing device 120 may obtain image data from the scanner 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

This description of the components of the imaging system herein are intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 130 may be a data storage including cloud computing platforms, such as public cloud, private cloud, community, and hybrid clouds, etc. However, those variations and modifications do not depart from the scope of the present disclosure.

Figure 2:
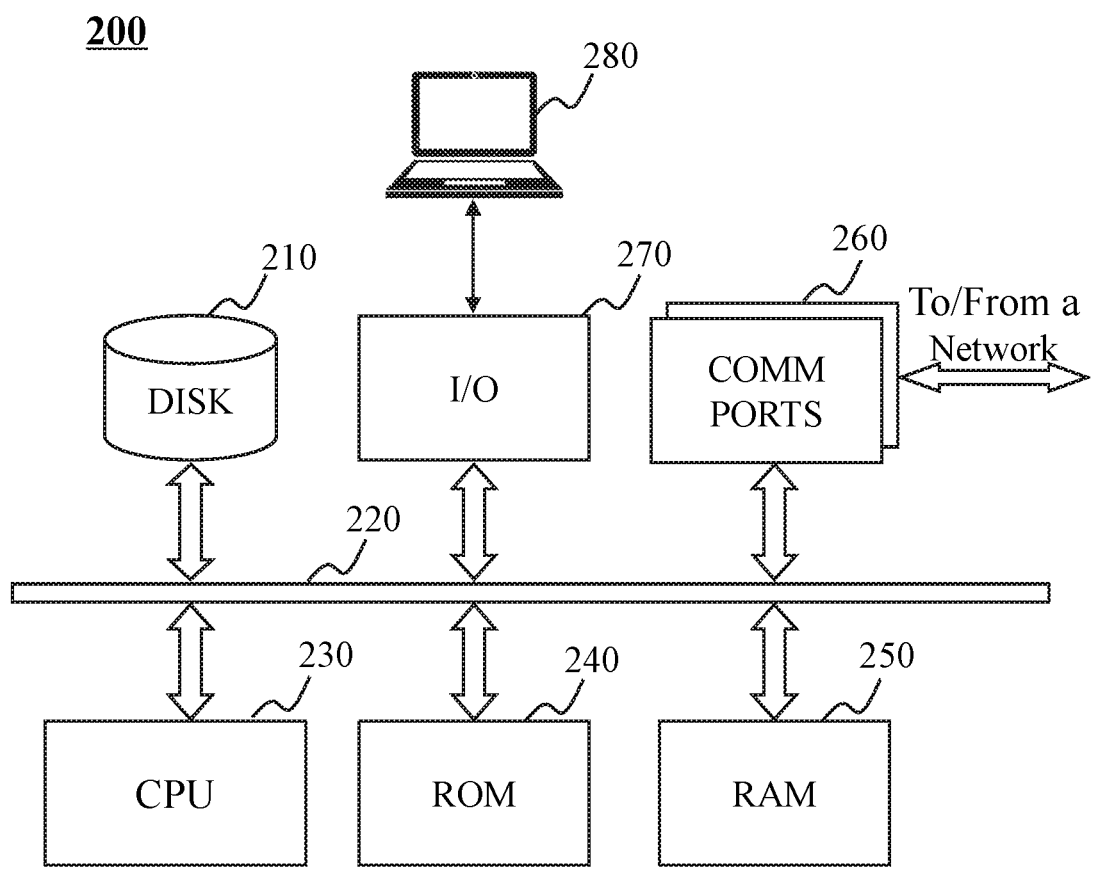
FIG. 2 is a schematic diagram illustrating an exemplary hardware and software components of a computing device on which processing device may be implemented according to some embodiments of the present disclosure.
Figure 4:
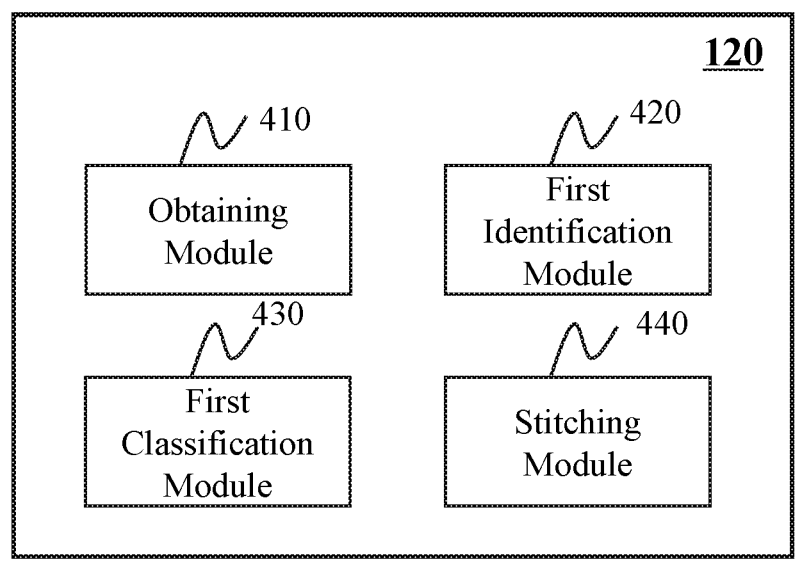
FIG. 4 is a block diagram illustrating an exemplary processing device according to some embodiments of the present disclosure.

FIG. 2 is a schematic diagram illustrating exemplary hardware and software components of a computing device on which a processing device may be implemented according to some embodiments of the present disclosure. For example, as illustrated in FIG. 4, an obtaining module 410, a first identification module 420, a first classification module 430 and/or a stitching module 440 may be implemented on the computing device 200 and configured to perform functions of the processing device 120 described in this disclosure.

The computing device 200 may be a general-purpose computer or a special-purpose computer; both may be used to implement some or all functions of the imaging system described in the present disclosure. For example, the imaging system may be implemented on the computing device 200, via its hardware, software program, firmware, or any combination thereof. Although only one such computer is shown, for convenience, the computer functions relating to the imaging system described herein may be implemented in a distributed fashion on a number of similar platforms, to distribute the processing load.

The computing device 200, for example, may include COM ports 260 connected to and from a network connected thereto to facilitate data communications. The computing device 200 may also include a central processing unit (CPU) 230, in the form of one or more processors, for executing program instructions. The exemplary computer platform may include an internal communication bus 220, program storage and data storage of different forms, for example, a disk 210, and a read-only memory (ROM) 240, or a random access memory (RAM) 250, for various data files to be processed and/or transmitted by the computer. The exemplary computer platform may also include program instructions stored in the ROM 240, RAM 250, and/or another type of non-transitory storage medium to be executed by the CPU 230. The methods and/or processes of the present disclosure may be implemented as the program instructions. The computing device 200 also includes an I/O component 270, supporting input/output between the computer and other components therein such as user interface elements 280. The computing device 200 may also receive programming and data via network communications.

Merely for illustration, only one CPU and/or processor is described in the computing device 200. However, it should be noted that the computing device 200 in the present disclosure may also include multiple CPUs and/or processors, thus operations and/or method steps that are performed by one CPU and/or processor as described in the present disclosure may also be jointly or separately performed by the multiple CPUs and/or processors. For example, if in the present disclosure the CPU and/or processor of the computing device 200 executes both operation A and operation B, it should be understood that operation A and operation B may also be performed by two different CPUs and/or processors jointly or separately in the computing device 200 (e.g., the first processor executes operation A and the second processor executes operation B, or the first and second processors jointly execute operations A and B).

Figure 3:
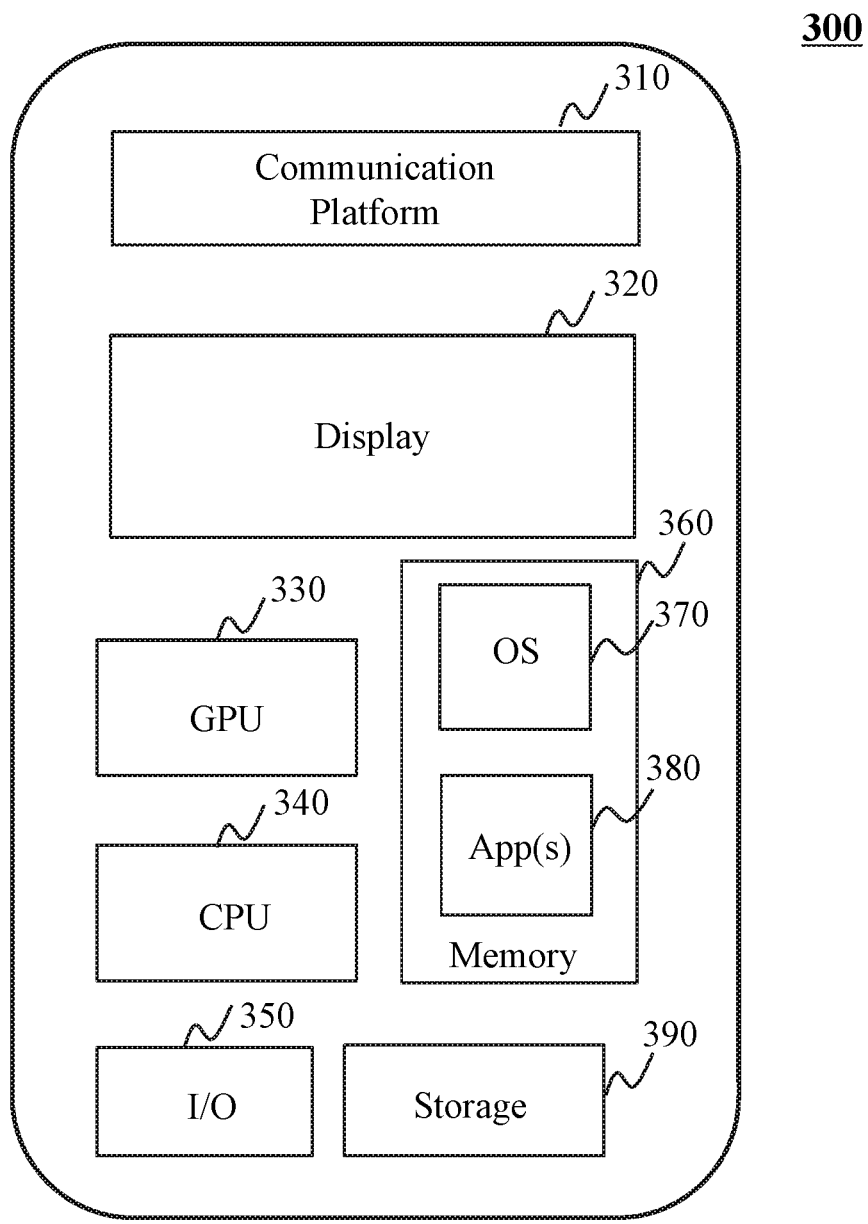
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device on which the terminal(s) may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information respect to image processing or other information from the processing device 120. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of workstation or external device. A computer may also act as a server if appropriately programmed.

FIG. 4 is a block diagram illustrating an exemplary processing device according to some embodiments of the present disclosure. The processing device 120 may include an obtaining module 410, a first identification module 420, a first classification module 430, and a stitching module 440. At least part of the processing device 120 may be implemented on the computing device as illustrated in FIG. 2 or the mobile device as illustrated in FIG. 3.

The obtaining module 410 may be configured to obtain a plurality of image series. Each of the plurality of image series may include one or more scanning images. In some embodiments, the scanner 110 may generate scan data according to a scan of a subject. The processing device 120 may obtain the scan data from the scanner 110 and generate the plurality of image series according to the scan data. The processing device 120 may produce an image series based on a scan and produce a plurality of image series based on multiple scans. The image series may be stored in a storage device (e.g., the storage device 130). The obtaining module 410 may obtain the plurality of image series from the storage device 130.

The first identification module 420 may be configured to determine tags of the plurality of image series. In some embodiments, the first identification module 420 may be configured to determine a tag of each of the plurality of image series. The tag may include at least one of: a protocol title, a specific mark, and a name format of an image series.

The first classification module 430 may be configured to classify the plurality of image series based on the tags of the plurality of image series. For example, the first classification module 430 may classify image series that have the same or substantially same tag into a group. As used herein, "substantially same" refers to that a similarity between each of the tags or sub-tags of the plurality of image series is larger than a threshold (e.g., 90%, 95%, 99%, etc.). In some embodiments, if the similarity is 100%, the "substantially same" means the "same" or "completely same". The first classification module 430 may classify the plurality of image series into multiple groups according to their tags. The first classification module 430 may further determine one or more groups of image series based on the classification. In some embodiments, the first classification module 430 may transmit the one or more groups of image series to the stitching module 440 for further processing. In some embodiments, the first classification module 430 may transmit the one or more groups of image series to the storage device 130. The one or more groups of image series may be stored in the storage device 130.

The stitching module 440 may be configured to stitch at least one image series of one of the one or more groups of image series. For example, there are three groups of image series, such as group A, group B, and group C. Each of these three groups may include one or more image series. The stitching module 440 may select at least one group of the three groups to stitch, such as the group A. In some embodiments, the stitching module 440 may also select at least one image series of the selected group to stitch, such as the image series D of group A. In some embodiments, the stitching module 440 may stitch the selected image series into a single image.

The stitching module 440 may stitch the at least one image series based on one or more image stitching algorithms. For example, the one or more stitching algorithms may include Genetic Algorithm (GA), Particle Swarm Optimization (PSO), Simulated Annealing Algorithm (SAA), Powell algorithm, downhill simplex method, Gradient Descent Algorithm, or the like, or any combination thereof.

Figure 5:
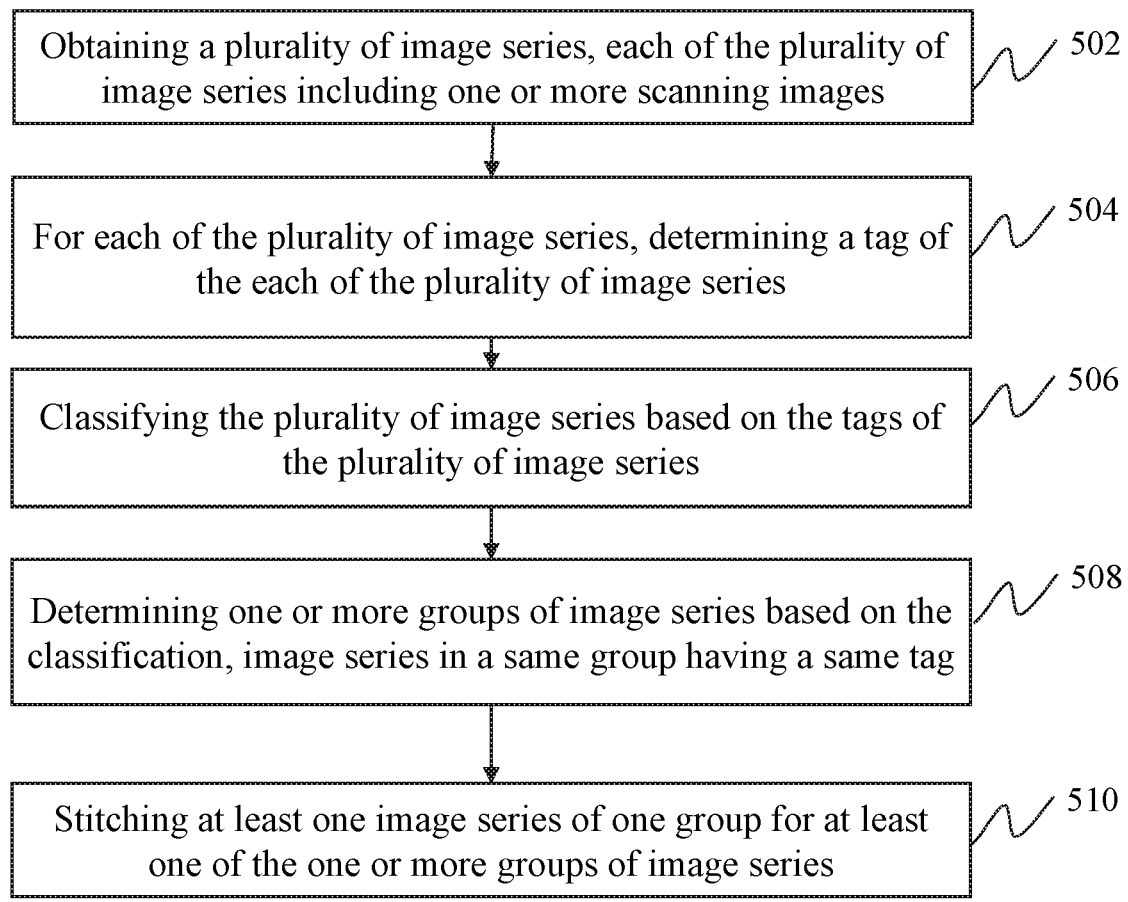
FIG. 5 is a flowchart illustrating an exemplary process for image processing according to some embodiments of the present disclosure.

FIG. 5 is a flowchart illustrating an exemplary process for image processing according to some embodiments of the present disclosure. In some embodiments, one or more operations of process 500 illustrated in FIG. 5 for image processing, and more particularly image stitching, may be implemented in the imaging system 100 illustrated in FIG. 1. For example, the process 500 may be stored in the storage device 130 in the form of instructions and be invoked and/or executed by the processing device 120 (e.g., the CPU 230 of the computing device 200 as illustrated in FIG. 2, the CPU 340 of the mobile device 300 as illustrated in FIG. 3). As another example, a portion of the process 500 may be implemented on the scanner 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 5 and described below is not intended to be limiting.

In 502, the processing device 120 (e.g., the obtaining module 410 of the processing device 120) may obtain a plurality of image series. Each of the plurality of image series may include one or more scanning images. In some embodiments, the scanner 110 may generate scan data according to a scan of a subject. The processing device 120 may obtain the scan data from the scanner 110 and generate the plurality of image series according to the scan data. The processing device 120 may produce an image series based on a scan and produce a plurality of image series based on multiple scans. In the present disclosure, the processing device 120 may stitch the plurality of image series to reconstruct a stitched image of the subject.

In 504, for each of the plurality of imaging series, the processing device 120 (e.g., the first identification module 420 of the processing device 120) may determine a tag of the each of the plurality of image series. In some embodiments, the tag may include at least one of the protocol title, the specific mark, and the name format of the each of the plurality of image series.

The protocol title refers to the title of a protocol used in the scan of the subject. In some embodiments, the protocol title may be determined according to the imaging method used in the scan of the subject. For example, for an MRI scan based on the longitudinal relaxation time (T1) and the fast spin echo (FSE) sequence, the protocol title may be represented by t1_fse. Similarly, for an MRI scan based on the transversal relaxation time (T2) and the fast spin echo (FSE) sequence, the protocol title may be represented by t2_fse; for an MRI scan based on the longitudinal relaxation time and the gradient reunite echo (GRE) sequence, the protocol title may be represented by t1_gre; for an MRI scan based on the transversal relaxation time and the gradient reunite echo sequence, the protocol title may be represented by t2_gre.

A specific mark refers to a mark, made by a user, on a scanning image. The specific mark may include one or more characters, icons, or the like, or any combination thereof. For example, the specific mark may be a text label "abcde" marking, which may be generated according to the input by a user, on an image of an image series. In some embodiments, the same type of images may have the same mark.

The name format refers to a name of a scanning image (e.g., an image of an image series). The user may customize the naming method of the scanning image. For example, the image may be named after the scanning date, such as 20170503112020.

In 506, the processing device 120 (e.g., the first classification module 430 of the processing device 120) may classify the plurality of image series based on the tags of the plurality of image series. In some embodiments, the image series having the same or substantially same tag may be classified into one group. As illustrated in 508, the processing device 120 may further determine one or more groups of image series based on the classification. Each of the one or more groups of image series may include one or more image series.

In some embodiments, the processing device 120 may perform data checking for the each of the one or more groups of image series. The data checking aims at determining whether the one or more groups of image series satisfy a requirement for further stitching. In response to satisfying the requirement for further stitching, the processing device 120 may proceed to operation 510. Otherwise, the processing device 120 may determine not to further stitching at least one of the one or more groups of image series. In this case, the processing device 120 may prompt information regarding the data checking for the user in various forms, such as, a message, an image, an audio, a video.

In some embodiments, the information regarding the data checking may include an unsuccessful data checking, a successful data checking, one or more reasons for the unsuccessful data checking, a yes-or-no question indicating further stitching. For example, the processing device 120 may direct a display (e.g., the display 280) to present information that indicates the unsuccessful data checking, the processing device 120 may determine not to perform the stitching as illustrated in 510. As another example, the processing device 120 may direct the display (e.g., the display 280) to present information that indicates the successful data checking, the processing device 120 may determine to perform the stitching as illustrated in 510. As a further example, the processing device 120 may direct the display (e.g., the display 280) to present the yes-or-no question indicating further stitching, if the user determines to further stitch (i.e., yes), the processing device 120 may determine to perform the stitching as illustrated in 510. Otherwise, the processing device 120 may determine not to perform the stitching as illustrated in 510.

In some embodiments, the processing device 120 may perform the data checking for one or more images including in the same image series of one group of the one or more groups of image series. The data checking may include checking whether one or more factors associated with the one or more images including in the same image series are consistent. As used herein, the one or more factors associated with the one or more images including in the same image series may be referred to as first factor(s). The first factor(s) may include a slice thickness, a slice gap, a pixel pitch, a filed of view (FOV), a scanning direction, a reference frame, or the like, or any combination thereof.

In some embodiments, the processing device 120 may perform the data checking for one or more images including in different image series of one group of the one or more groups of image series. The data checking may include checking whether one or more factors associated with the different image series of one group of the one or more groups of image series are consistent. As used herein, the one or more factors associated with the different image series of one group of the one or more groups of image series may be referred to as second factor(s). The second factor(s) may include a slice thickness, a slice gap, a pixel pitch, reference coordinates, a view orientation, a correction method for an image deformity, or the like, or any combination thereof. In some embodiments, the correction method for an image deformity may include a gray histogram-based correction method, a differential operator-based correction method, or the like, or any combination thereof.

In 510, the processing device 120 (e.g., the stitching module 440 of the processing device 120) may stitch at least one image series of one group, among the at least one of the one or more groups of image series, into a single image. In some embodiments, the processing device 120 may stitch the at least one image series based on one or more image stitching algorithms. For example, the one or more stitching algorithms may include Genetic Algorithm (GA), Particle Swarm Optimization (PSO), Simulated Annealing Algorithm (SAA), Powell algorithm, downhill simplex method, Gradient Descent Algorithm, or the like, or any combination thereof.

In some embodiments, the processing device 120 (e.g., the stitching module 440 of the processing device 120) may output the image series included in the group without the stitching operation if a group includes only one image series.

In some embodiments, the processing device 120 may stitch all image series of a group into a single image. In some embodiments, the user may select one or more image series of a group among the at least one of the one or more groups of image series. The processing device 120 may stitch the image series selected by the user into a single image. More detail descriptions about the stitching operation can be found elsewhere in this application (e.g., FIGS. 7-10, and the descriptions thereof).

It should be noted that the description of the process 500 is provided for the purposes of illustration and not intended to limit the scope of the present disclosure. For persons having ordinary skills in the art, various variations and modifications may be conducted under the teaching of the present disclosure. However, those variations and modifications do not depart from the scope of the present disclosure. For example, operations 506 and 508 may be integrated into one single operation. As another example, after the operation 506, the data checking may be omitted, and the operation 508 may be performed directly.

Figure 6:
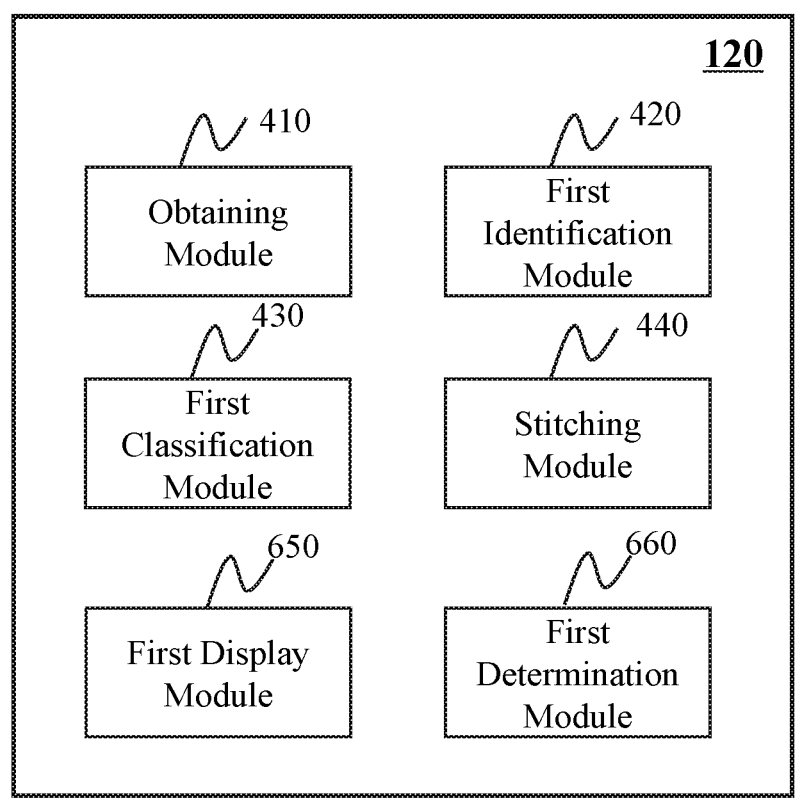
FIG. 6 is a block diagram illustrating an exemplary processing device according to some embodiments of the present disclosure.

FIG. 6 is a block diagram illustrating an exemplary processing device according to some embodiments of the present disclosure. The processing device 120 may not only include components as illustrated in FIG. 4, such as the obtaining module 410, the first identification module 420, the first classification module 430 and the stitching module 440, but also a first display module 650 and a first determination module 660. At least a portion of the processing device 120 may be implemented on the computing device as illustrated in FIG. 2 or the mobile device as illustrated in FIG. 3. The descriptions about the obtaining module 410, the first identification module 420, the first classification module and the stitching module 440 may be found elsewhere in this disclosure (e.g., FIG. 4 and the descriptions thereof).

The first display module 650 may be configured to display a plurality of stitching algorithms. The first display module 650 may display the plurality of stitching algorithms on a display, and a user may choose a suitable stitching algorithm to stitch the image series. Exemplary stitching algorithms may include but not limited to Genetic Algorithm (GA), Particle Swarm Optimization (PSO), Simulated Annealing Algorithm (SAA), Powell algorithm, downhill simplex method, Gradient Descent Algorithm, or the like, or any combination thereof.

The first determination module 660 may be configured to receive, by an input device, one or more instructions from the user, and determine a stitching algorithm based on the one or more instructions. The input instructions received through the input device may be transmitted to the first determination module 660 via, for example, a bus 220, for determining a stitching algorithm. The one or more instructions may be used to specify a stitching algorithm for image stitching. The one or more instructions may be in various forms, such as an audio instruction, a video instruction, a character instruction.

The input device may include alphanumeric keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc.

Figure 7:
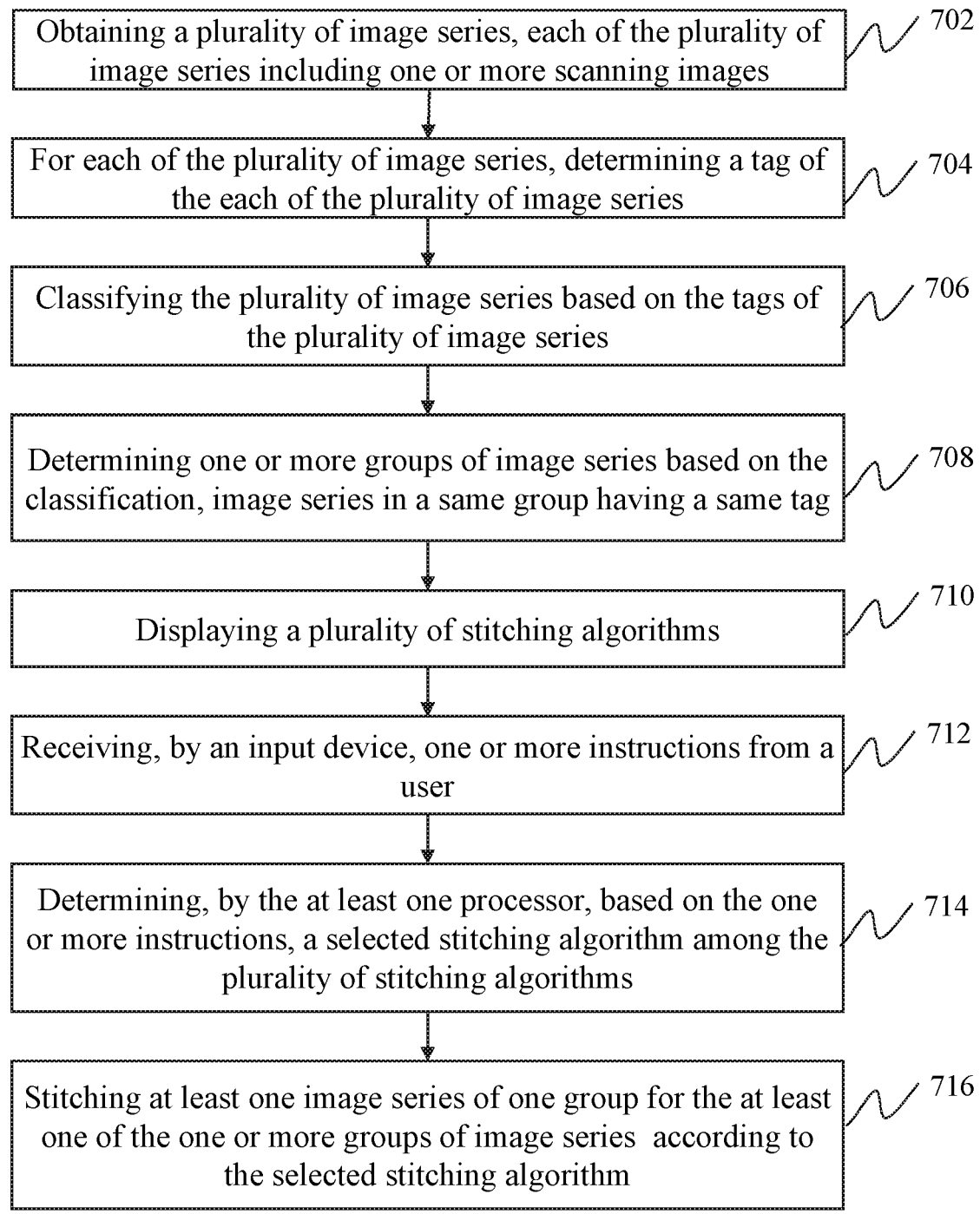
FIG. 7 is a flowchart illustrating an exemplary process for image processing according to some embodiments of the present disclosure.

FIG. 7 is a flowchart illustrating an exemplary process for image processing according to some embodiments of the present disclosure. In some embodiments, one or more operations of process 700 as illustrated in FIG. 7 for image processing, more particularly, image stitching, may be implemented in the imaging system 100 illustrated in FIG. 1. For example, the process 700 may be stored in the storage device 130 in the form of instructions and be invoked and/or executed by the processing device 120 (e.g., the CPU 230 of the computing device 200 as illustrated in FIG. 2, the CPU 340 of the mobile device 300 as illustrated in FIG. 3). As another example, one or more operations of the process 700 may be implemented on the scanner 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 7 and described below is not intended to be limiting.

Operations 702-708 may be similar to operations 502-508 of the process 500 described above, the detailed descriptions of which may be found in this disclosure in connection with FIG. 5.

In 710, the processing device 120 (e.g., the first display module 650 of the processing device 120) may display a plurality of stitching algorithms on a display (e.g., a LED display, an OLED display). The stitching results of the image series may be different with different stitching algorithms. In some embodiments, one stitching algorithm may not be suitable for stitching different types of image series. The processing device 120 may display the plurality of stitching algorithms on a display, and the user may choose a suitable stitching algorithm to stitch the image series. Exemplary stitching algorithms may include but not limited to Genetic Algorithm (GA), Particle Swarm Optimization (PSO), Simulated Annealing Algorithm (SAA), Powell algorithm, downhill simplex method, Gradient Descent Algorithm, or the like, or any combination thereof. In some embodiments, one of the plurality of stitching algorithms may be set as a default stitching algorithm for image stitching.

In 712, the processing device 120 (e.g., the first determination module 660 of the processing device 120) may receive, by an input device, one or more instructions from the user. The one or more instructions may be used to specify a stitching algorithm for image stitching. The one or more instructions may be in various forms, such as an audio instruction, a video instruction, a character instruction. Furthermore, as illustrated in 714, the processing device 120 (e.g., the first determination module 660 of the processing device 120) may determine a stitching algorithm among the plurality of stitching algorithms based on the one or more instructions. For example, the user may select GA algorithm for stitching the image series. In some embodiments, operations 710-714 may be performed before stitching at least one image series of at least one group of the one or more groups of image series.

In 716, the processing device 120 (e.g., the stitching module 440 of the processing device 120) may stitch at least one image series of one group for the at least one of the one or more groups of image series according to the selected stitching algorithm. In some embodiments, the processing device 120 may stitch all image series of one group for the at least one of the one or more groups of image series. Merely by way of example, if group A of image series is one of the one or more of groups of image series, the user may select group A of image series to stitch. The group A may include one or more image series. A stitching algorithm may be selected according to the instructions form the user (e.g., the user selects the GA algorithm). The processing device 120 may stitch all image series of group A based on the selected algorithm into a single image. In some embodiments, the processing device 120 may stitch a selected image series of the group for the at least one of the one or more groups of image series. For example, if group A may include three image series, which may be represented by T1, T2, T3, respectively. Series T2 and T3 are selected for stitching. Then the processing device 120 may stitch series T2 and T3 into a single image based on the selected algorithm (e.g., GA algorithm). In some embodiments, the processing device 120 may stitch any combination of the image series of the group for the at least one of the one or more groups of image series. The image series may be combined based on a permutation method (e.g., $C_n^m$). For example, if group A may include three image series, which may be represented by T1, T2, T3, respectively. There are three combinations for the image series of group A (i.e., T1T2, T1T3, T2T3). The processing device 120 may stitch any one of the three combinations into a single image. It should be noted that, the processing device 120 may output the image series included in the group without the stitching operation if a group includes only one image series.

In some embodiments, before stitching the at least one image series of at least one group of the one or more groups of image series, the processing device 120 may perform the data checking for the at least one image series of at least one group of the one or more groups of image series. The data checking is similar to the above description of the data checking as illustrated in FIG. 5, and not repeated herein.

It should be noted that the descriptions of the process 700 are provided for the purposes of illustration and not intended to limit the scope of the present disclosure. For persons having ordinary skills in the art, various variations and modifications may be conducted under the teaching of the present disclosure. However, those variations and modifications do not depart from the scope of the present disclosure. For example, operations 712 and 714 may be integrated into one single operation.

Figure 8:
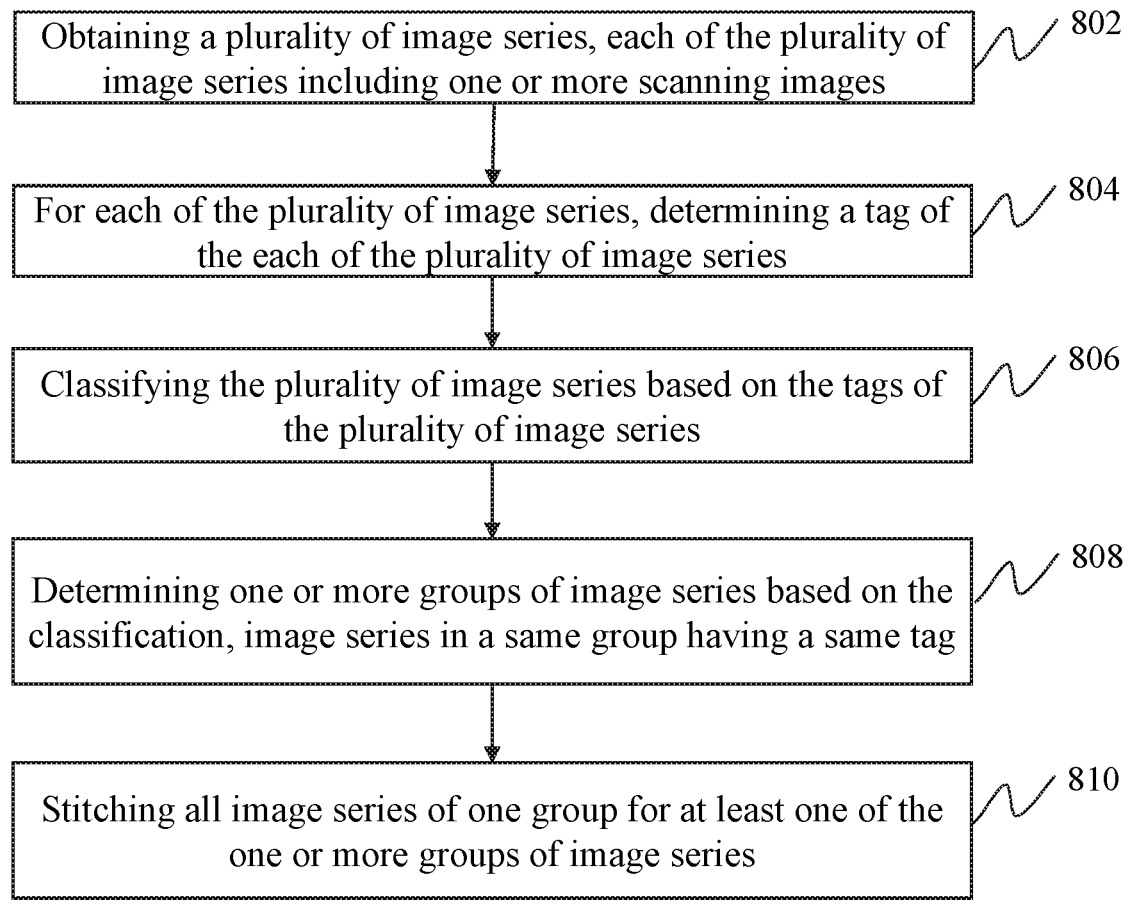
FIG. 8 is a flowchart illustrating an exemplary process for image processing according to some embodiments of the present disclosure.

FIG. 8 is a flowchart illustrating an exemplary process for image processing according to some embodiments of the present disclosure. In some embodiments, one or more operations of process 800 as illustrated in FIG. 8 for image processing, and more particularly image stitching, may be implemented in the imaging system 100 illustrated in FIG. 1. For example, the process 800 may be stored in the storage device 130 in the form of instructions and be invoked and/or executed by the processing device 120 (e.g., the CPU 230 of the computing device 200 as illustrated in FIG. 2, the CPU 340 of the mobile device 300 as illustrated in FIG. 3). As another example, one or more operations of the process 800 may be implemented on the scanner 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 8 and described below is not intended to be limiting.

Operations 802-808 may be similar to operations 502-508 of the process 500 and/or operations 702-708 of the process 700 described above, the detailed descriptions of which may be found in this disclosure in connection with FIGS. 5 and 7.

In 810, the processing device 120 (e.g., the stitching module 440 of the processing device 120) may stitch all image series of one group among the one or more groups of image series based on one or more image stitching algorithms. For example, a user may select group A of image series to stitch. The group A may include one or more image series. The processing device 120 may stitch all image series of group A based on the one or more stitching algorithms into a single image.

In some embodiments, the processing device 120 may stitch all image series of the group among the one or more groups of image series based on the one or more stitching algorithms without an input from the user for selecting a stitching algorithm. For example, upon receiving an instruction relating to executing operating 808, the processing device 120 may automatically stitch all image series of the group based on a default stitching algorithm. The default stitching algorithm may be predetermined by the user or the processing device 120. In some embodiments, the processing device 120 may stitch all the image series of the group based on other stitching algorithm selected by the user.

In some embodiments, before stitch all image series of one group among the one or more groups of image series, the processing device 120 may perform the data checking for all image series of one group among the one or more groups of image series. The data checking is similar to the above description of the data checking as illustrated in FIG. 5, and not repeated herein.

It should be noted that the description of the process 700 is provided for the purposes of illustration and not intended to limit the scope of the present disclosure. For persons having ordinary skills in the art, various variations and modifications may be conducted under the teaching of the present disclosure. However, those variations and modifications do not depart from the scope of the present disclosure. For example, operations 806 and 808 may be integrated into one single operation. As another example, before the operation 810, the data checking may be omitted.

Figure 9:
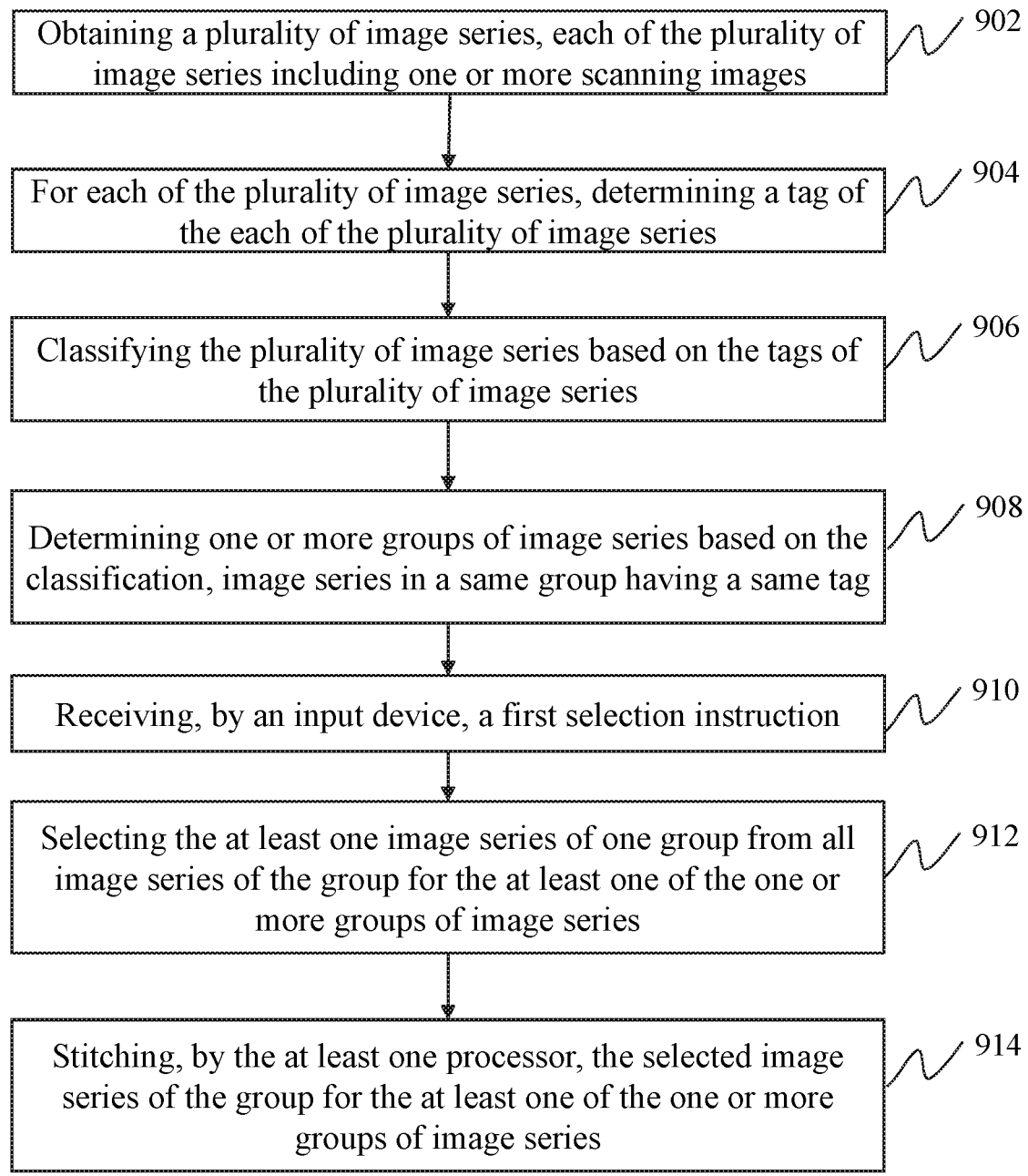
FIG. 9 is a flowchart illustrating an exemplary process for image processing according to some embodiments of the present disclosure.

FIG. 9 is a flowchart illustrating an exemplary process for image processing according to some embodiments of the present disclosure. In some embodiments, one or more operations of process 900 as illustrated in FIG. 9 for image processing, more particularly, image stitching, may be implemented in the imaging system 100 illustrated in FIG. 1. For example, the process 900 may be stored in the storage device 130 in the form of instructions and be invoked and/or executed by the processing device 120 (e.g., the CPU 230 of the computing device 200 as illustrated in FIG. 2, the CPU 340 of the mobile device 300 as illustrated in FIG. 3). As another example, one or more operations of the process 900 may be implemented on the scanner 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 9 and described below is not intended to be limiting.

Operations 902-908 may be similar to operations 502-508 of the process 500 and/or operations 702-708 of the process 700 described above, the detailed descriptions of which may be found in this disclosure in connection with FIGS. 5 and 7.

In 910, the processing device 120 (e.g., the stitching module 440 of the processing device 120) may receive a first selection instruction from a user via an input device. The first instruction may be used to select at least one image series. The first instruction may be in various forms, such as an audio instruction, a video instruction, a character instruction. As illustrated in 912, the processing device 120 may select at least one image series of one group from all image series of the group based on the first selection instruction.

Furthermore, as illustrated in 914, the processing device 120 (e.g., the stitching module 440) may stitch the selected image series into a single image based on one or more stitching algorithms.

For example, group A may include three image series. The three image series may be represented by T1, T2, T3, respectively. The user may input the first selection instruction (e.g., an audio instruction) by the input device (e.g., an audio sensor) for selecting series T2 and T3 to be stitched. Then the processing device 120 (e.g., the stitching module 440 of the processing device 120) may stitch the selected image series T2 and T3 into a single image based on the stitching algorithm(s).

In some embodiments, before stitching the selected image series, the processing device 120 may perform the data checking for the selected image series. The data checking is similar to the above description of the data checking as illustrated in FIG. 5, and not repeated herein.

It should be noted that the description of the process 900 is provided for the purposes of illustration and not intended to limit the scope of the present disclosure. For persons having ordinary skills in the art, various variations and modifications may be conducted under the teaching of the present disclosure. However, those variations and modifications do not depart from the scope of the present disclosure. For example, operations 904 and 906 may be integrated into one single operation. As another example, operations 910 and 912 may be integrated into one single operation. As a further example, before the operation 810, the data checking may be omitted.

Figure 10:
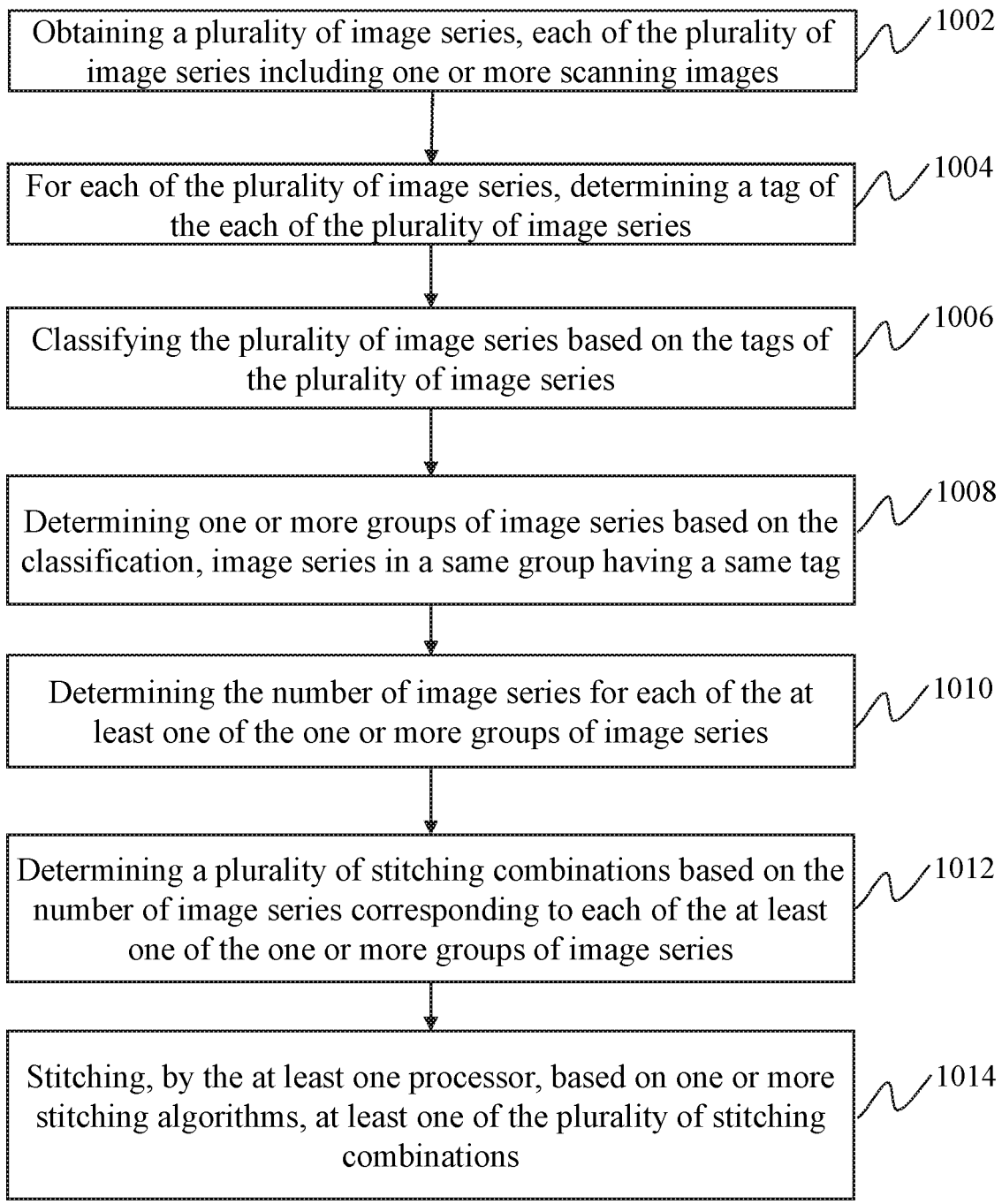
FIG. 10 is a flowchart illustrating an exemplary process for image processing according to some embodiments of the present disclosure.

FIG. 10 is a flowchart illustrating an exemplary process for image processing according to some embodiments of the present disclosure. In some embodiments, one or more operations of process 1000 as illustrated in FIG. 10 for image processing, more particularly, image stitching, may be implemented in the imaging system 100 illustrated in FIG. 1. For example, the process 1000 may be stored in the storage device 130 in the form of instructions and be invoked and/or executed by the processing device 120 (e.g., the CPU 230 of the computing device 200 as illustrated in FIG. 2, the CPU 340 of the mobile device 300 as illustrated in FIG. 3). As another example, one or more operations of the process 1000 may be implemented on the scanner 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 10 and described below is not intended to be limiting.

Operations 1002-1008 may be similar to operations 502-508 of the process 500 and/or operations 702-708 of the process 700 described above, the detailed descriptions of which may be found in this disclosure in connection with FIGS. 5 and 7.

In 1010, the processing device 120 (e.g., the stitching module 440 of the processing device 120) may determine the number of image series for each of the at least one of the one or more groups of image series. Furthermore, as illustrated in 1012, the processing device 120 may determine a plurality of stitching combinations based on the number of image series corresponding to each of the at least one of the one or more groups of image series. In some embodiments, the stitching combinations of the image series may be determined based on a permutation method. Exemplary permutation method may be represented by Equation (1) as follows:

$$C_n^m = \frac{n!}{(n-m)!m!}, \qquad (1)$$

where n denotes the number of image series for each of the at least one of the one or more groups of image series, m denotes the number of image series of stitching combinations corresponding to each of the at least one of the one or more groups of image series. In some embodiments, $1<m\leq n$. Merely by way of example, the image series of group A may be selected to stitch, the number n of the image series of group A is 4. The image series of group A may be represented by A1, A2, A3, A4, respectively. The number m of the image series of the stitching combinations corresponding to group A may be 2, 3, or 4. Then the total number of the stitching combinations may be 11, i.e., $C_4^2+C_4^3+C_4^4=11$. The stitching combinations may include A1A2, A1A3, A1A4, A2A3, A2A4, A3A4, A1A2A3, A1A2A4, A1A3A4, A2A3A4, A1A2A3A4.

In 1014, the processing device 120 (e.g., the stitching module 440 of the processing device 120) may stitch at least one of the plurality of stitching combinations based on one or more stitching algorithms. For example, the processing device 120 may stitch the image series included in A1A3, A1A4, A2A3, etc.

It should be noted that the description of the process 1000 is provided for the purposes of illustration and not intended to limit the scope of the present disclosure. For persons having ordinary skills in the art, various variations and modifications may be conducted under the teaching of the present disclosure. However, those variations and modifications do not depart from the scope of the present disclosure. For example, operations 1004 and 1006 may be integrated into one single operation. As another example, operations 1010 and 1012 may be integrated into one single operation.

Figure 11:
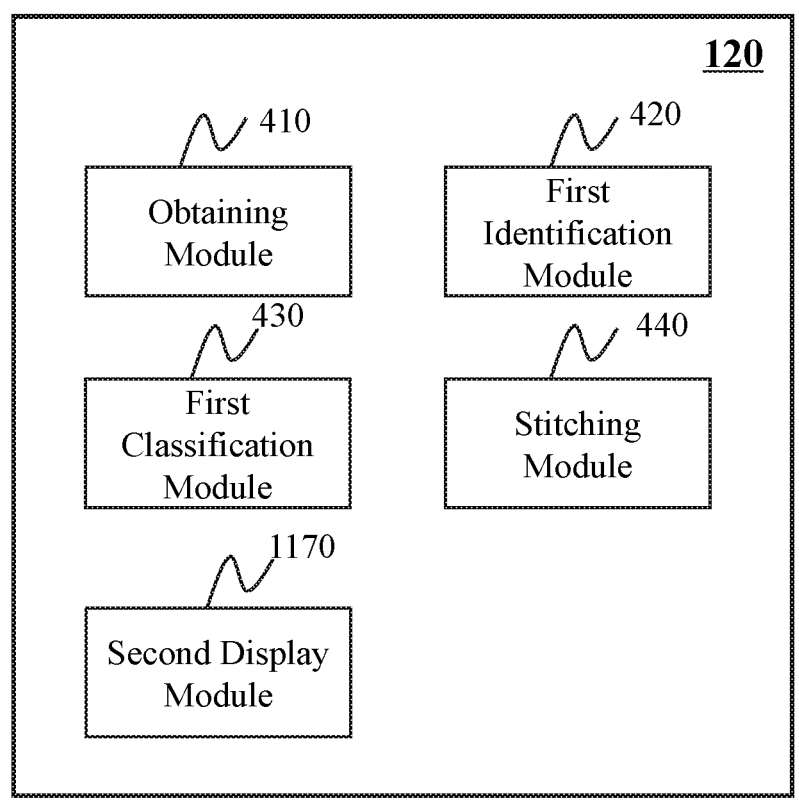
FIG. 11 is a block diagram illustrating an exemplary processing device according to some embodiments of the present disclosure.

FIG. 11 is a block diagram illustrating an exemplary processing device 120 according to some embodiments of the present disclosure. The processing device 120 may not only include components as illustrated in FIG. 4, but also include a second display module 1170. At least a portion of the processing device 120 may be implemented on the computing device as illustrated in FIG. 2 or the mobile device as illustrated in FIG. 3.

The second display module 1170 may be configured to display a stitching result by a display. More particularly, the second display module 1170 may receive the stitching result from the stitching module 440 and display the stitching result. The stitching result may include the stitching result of all image series of one group, the stitching result of the selected image series of the group, the stitching result of each of the plurality of stitching combinations, etc. Examples of the display may include a liquid crystal display (LCD), a light-emitting diode (LED)-based display, a flat panel display, a curved screen, a television device, a cathode ray tube (CRT), a touch screen, or the like, or a combination thereof.

Figure 12:
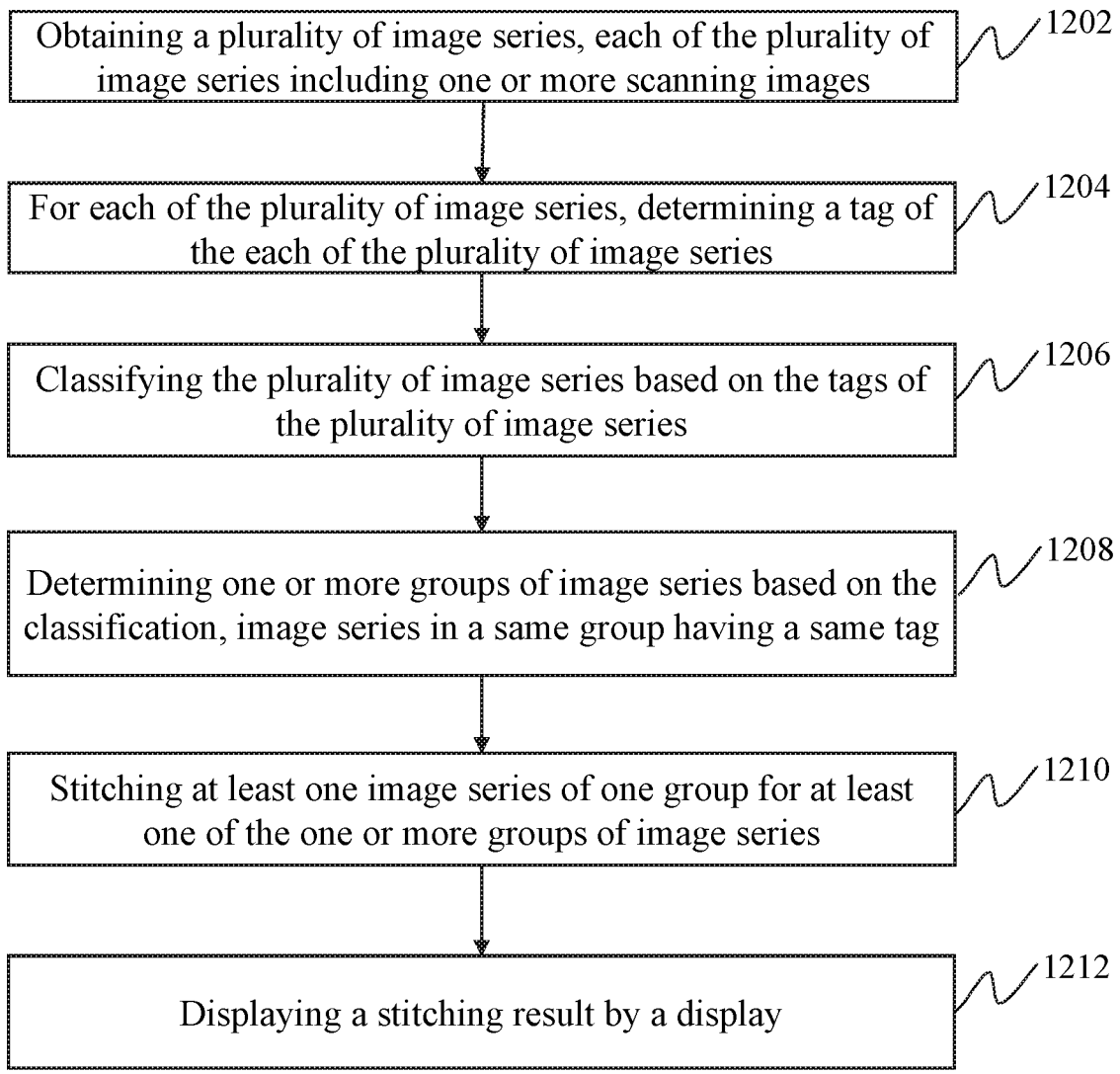
FIG. 12 is a flowchart illustrating an exemplary process for image processing according to some embodiments of the present disclosure.

FIG. 12 is a flowchart illustrating an exemplary process for image processing according to some embodiments of the present disclosure. In some embodiments, one or more operations of process 1200 as illustrated in FIG. 12 for image processing, more particularly, image stitching, may be implemented in the imaging system 100 illustrated in FIG. 1. For example, the process 1200 may be stored in the storage device 130 in the form of instructions and be invoked and/or executed by the processing device 120 (e.g., the CPU 230 of the computing device 200 as illustrated in FIG. 2, the CPU 340 of the mobile device 300 as illustrated in FIG. 3). As another example, one or more operations of the process 1200 may be implemented on the scanner 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 12 and described below is not intended to be limiting.

Operations 1202-1210 may be similar to operations 502-508 of the process 500 described above, the detailed descriptions of which may be found in this disclosure in connection with FIG. 5. In some embodiments, after the stitching, the processing device 120 (e.g., the second display module 1170 of the processing device 120) may display a stitching result by a display.

In 1212, the processing device 120 (e.g., the second display module 1170 of the processing device 120) may display a stitching result by a display. In some embodiments, the stitching module 440 may determine the stitching result. The stitching result may include the stitching result of all image series of one group, the stitching result of the selected image series of the group, the stitching result of each of the plurality of stitching combinations, etc. In some embodiments, the processing device 120 may display the stitching result in real time. For example, when the stitching module 440 stitches the image series of a first group (group A), the second display module 1170 may display the stitching result in real time. If there are image series of other groups (e.g., group B, group C) to be stitched, the stitching process may be performed in the background of the imaging system 100, so as to avoid affecting other operation of the user (e.g., zoom in or zoom out for the stitching result). In some embodiments, if there are a plurality of stitching results for the image series, the stitching results may be displayed according to the user setting. For example, the user setting may include displaying two or more stitching results at the same time.

It should be noted that the description of the process 1200 is provided for the purposes of illustration and not intended to limit the scope of the present disclosure. For persons having ordinary skills in the art, various variations and modifications may be conducted under the teaching of the present disclosure. However, those variations and modifications do not depart from the scope of the present disclosure. For example, operations 1206 and 1208 may be integrated into one single operation.

Figure 13:
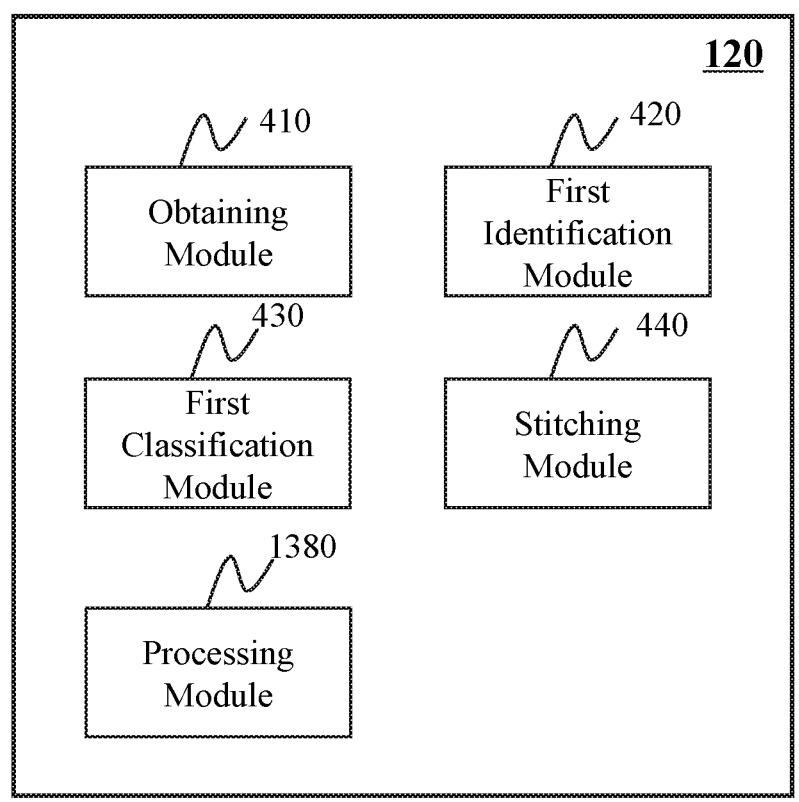
FIG. 13 is a block diagram illustrating an exemplary processing device according to some embodiments of the present disclosure.

FIG. 13 is a block diagram illustrating an exemplary processing device 120 according to some embodiments of the present disclosure. The processing device 120 may not only include components as illustrated in FIG. 4, such as the obtaining module 410, the first identification module 420, the first classification module 430 and the stitching module 440, but also a processing module 1380. At least a portion of the processing device 120 may be implemented on the computing device as illustrated in FIG. 2 or the mobile device as illustrated in FIG. 3. The descriptions about the obtaining module 410, the first identification module 420, the first classification module 430 and the stitching module 440 may be found described elsewhere in this disclosure (e.g., FIG. 4 and the descriptions thereof).

The processing module 1380 may be further configured to display one or more stitched image series in the form of a list. For example, there are 10 stitching results for the image series. The processing module 1380 may display the 10 stitching results in the form of the list. In some embodiments, the stitching results may be arranged according to the stitching time. For example, the stitching result may be displayed based on descending order or ascending order of the stitching time.

Figure 14:
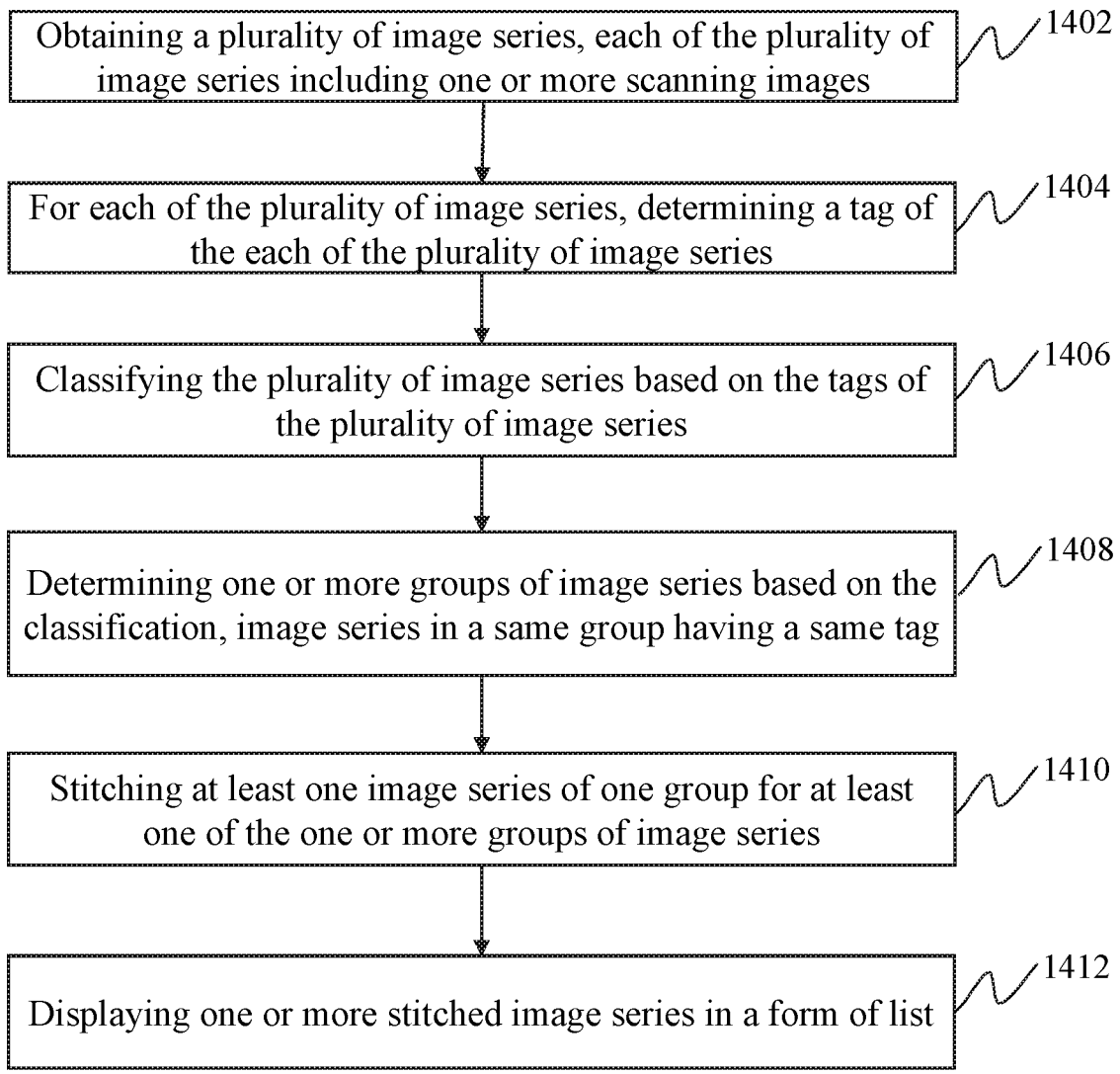
FIG. 14 is a flowchart illustrating an exemplary process for image processing according to some embodiments of the present disclosure.

FIG. 14 is a flowchart illustrating an exemplary process for image processing according to some embodiments of the present disclosure. In some embodiments, one or more operations of process 1400 as illustrated in FIG. 14 for image processing, and more particularly image stitching, may be implemented in the imaging system 100 illustrated in FIG. 1. For example, the process 1400 may be stored in the storage device 130 in the form of instructions and be invoked and/or executed by the processing device 120 (e.g., the CPU 230 of the computing device 200 as illustrated in FIG. 2, the CPU 340 of the mobile device 300 as illustrated in FIG. 3). As another example, one or more operations of the process 1400 may be implemented on the scanner 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 14 and described below is not intended to be limiting.

Operations 1402-1410 may be similar to operations 502-508 of the process 500 and/or operations 702-708 of the process 700 described above, the detailed descriptions of which may be found in this disclosure in connection with FIGS. 5 and 7.

In 1412, the processing device 120 (e.g., the processing module 1380) may display one or more stitched image series in the form of a list. After finishing stitching process (i.e., operations 1402-1410 as illustrated in FIG. 14), the processing module 1380 may display each of a plurality of stitched image series in the form of a list. The user may check any one of the stitched image series displayed in the list. It should be noted that the stitched image series may be displayed in various forms, such as a thumbnail, a folder, etc.

It should be noted that the description of the process 1400 is provided for the purposes of illustration and not intended to limit the scope of the present disclosure. For persons having ordinary skills in the art, various variations and modifications may be conducted under the teaching of the present disclosure. However, those variations and modifications do not depart from the scope of the present disclosure. For example, operations 1406 and 1408 may be integrated into one single operation.

Figure 15:
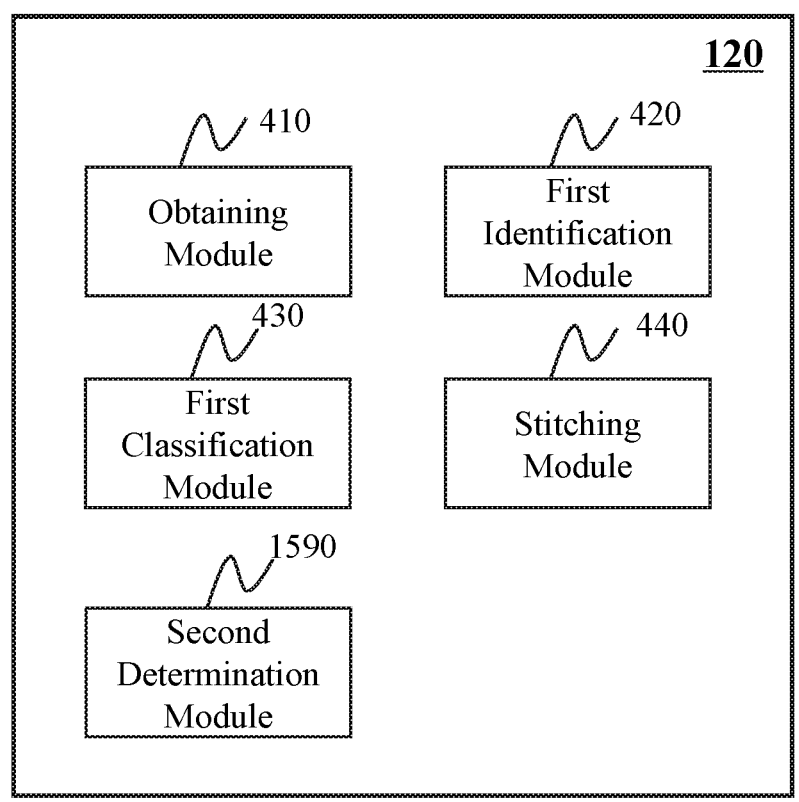
FIG. 15 is a block diagram illustrating exemplary processing device according to some embodiments of the present disclosure.

FIG. 15 is a block diagram illustrating an exemplary processing device 120 according to some embodiments of the present disclosure. The processing device 120 may not only include components as illustrated in FIG. 4, such as the obtaining module 410, the first identification module 420, the first classification module 430 and the stitching module 440, but also a second determination module 1590. At least a portion of the processing device 120 may be implemented on the computing device as illustrated in FIG. 2 or the mobile device as illustrated in FIG. 3. The descriptions about the obtaining module 410, the first identification module 420, the first classification module 430 and the stitching module 440 may be found described elsewhere in this disclosure (e.g., FIG. 4 and the descriptions thereof).

The second determination module 1590 may be configured to receive a second selection instruction from a user to determine one or more specific groups among the one or more groups of image series in response to receiving the second selection instruction. The second selection instruction may be used to select the one or more specific groups by an input device. The second selection instruction may exist in various forms, such as an audio instruction, a video instruction, a character instruction. The input device may include alphanumeric keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc.

Figure 16:
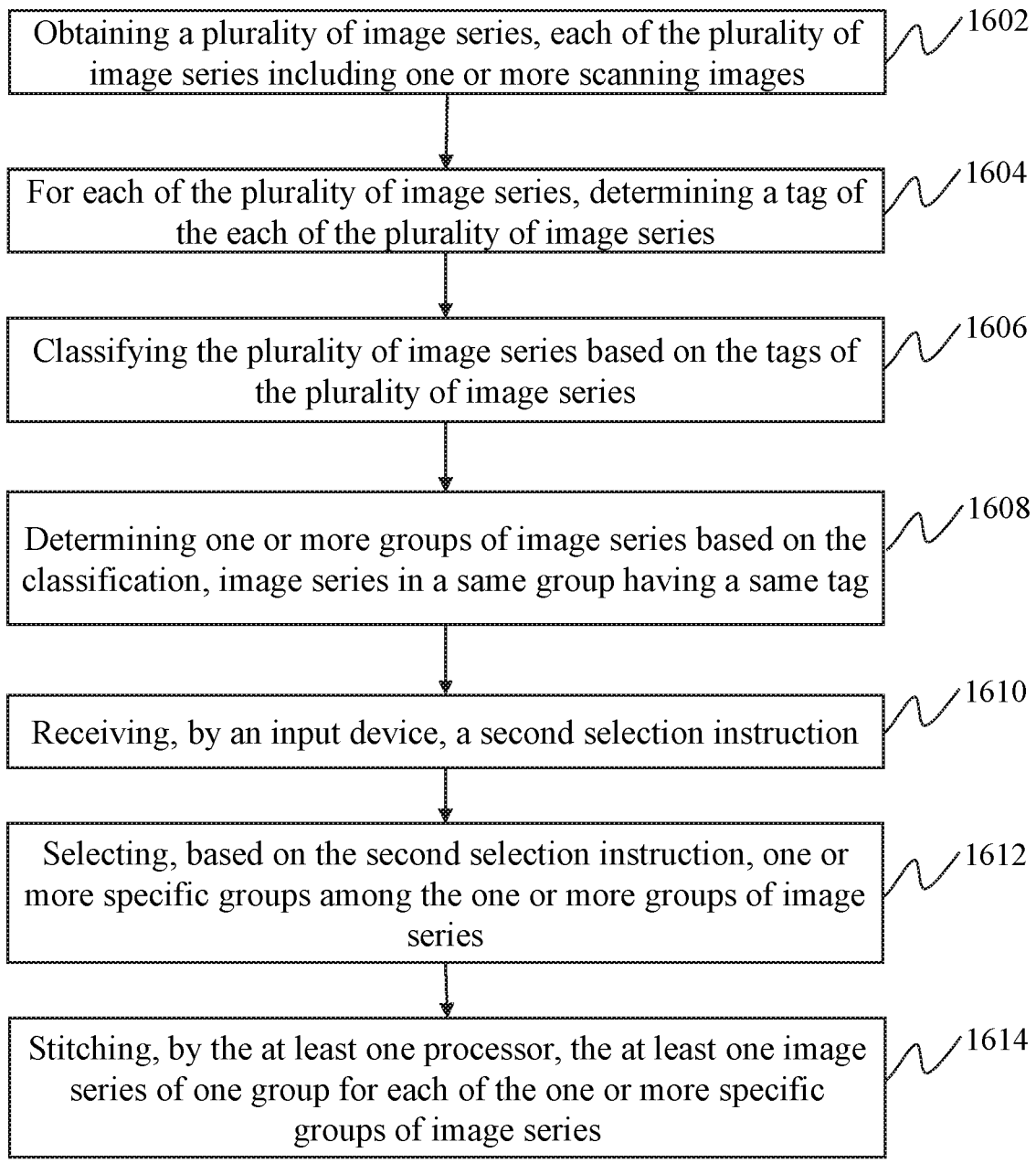
FIG. 16 is a flowchart illustrating an exemplary process for image processing according to some embodiments of the present disclosure.

FIG. 16 is a flowchart illustrating an exemplary process for image processing according to some embodiments of the present disclosure. In some embodiments, one or more operations of process 1600 as illustrated in FIG. 16 for image processing, more particularly, image stitching, may be implemented in the imaging system 100 illustrated in FIG. 1. For example, the process 1600 may be stored in the storage device 130 in the form of instructions and be invoked and/or executed by the processing device 120 (e.g., the CPU 230 of the computing device 200 as illustrated in FIG. 2, the CPU 340 of the mobile device 300 as illustrated in FIG. 3). As another example, one or more operations of the process 1600 may be implemented on the scanner 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 16 and described below is not intended to be limiting.

Operations 1602-1608 may be similar to operations 502-508 of the process 500 and/or operations 702-708 of the process 700 described above, the detailed descriptions of which may be found in this disclosure in connection with FIGS. 5 and 7.

In 1610, the processing device 120 (e.g., the second determination module 1590 of the processing device 120) may receive a second selection instruction by an input device. The second instructions may be used to select one or more specific groups among the one or more groups of image series. The second instruction may exist in various forms, such as an audio instruction, a video instruction, a character instruction. As illustrated in 1612, the processing device 120 may select one or more specific groups among the one or more groups of image series based on the second instructions. For example, there are 10 groups of image series determined based on the classification. The user may input the second instruction, such as selecting 3 groups among the 10 groups (e.g., group A, group B, group C), into the second determination module 1590. These selected groups (i.e., group A, group B, group C) may be designated as the specific groups. In some embodiments, it should be understood that operations 1610-1612 may be performed before stitching at least one image series of one group for each of the specific groups of image series. The processing device 120 (e.g., the stitching module 440) may further stitch at least one image series of one group for each of the specific groups of image series, as illustrated in 1614. Each of the specific groups of image series may include one or more image series. In some embodiments, at least one image series included in the specific groups of image series may be selected to stitch. For example, the stitching module 440 may stitch both series T1 and T2, included in the specific group A, into a single image. As another example, the stitching module 440 may stitch series T1 included in the specific group A and series T3 included in the specific group B into a single image. It should be noted that if there is only one image series included in a specific group, the processing device 120 may output the image series directly without stitching.

In some embodiments, before stitching the at least one image series of one group for each of the specific groups of image series, the processing device 120 may perform the data checking for each of the specific groups of image series. The data checking is similar to the above description of the data checking as illustrated in FIG. 5, and not repeated herein.

It should be noted that the description of the process 1600 is provided for the purposes of illustration and not intended to limit the scope of the present disclosure. For persons having ordinary skills in the art, various variations and modifications may be conducted under the teaching of the present disclosure. However, those variations and modifications do not depart from the scope of the present disclosure. For example, operations 1610 and 1612 may be integrated into one single operation.

Figure 17:
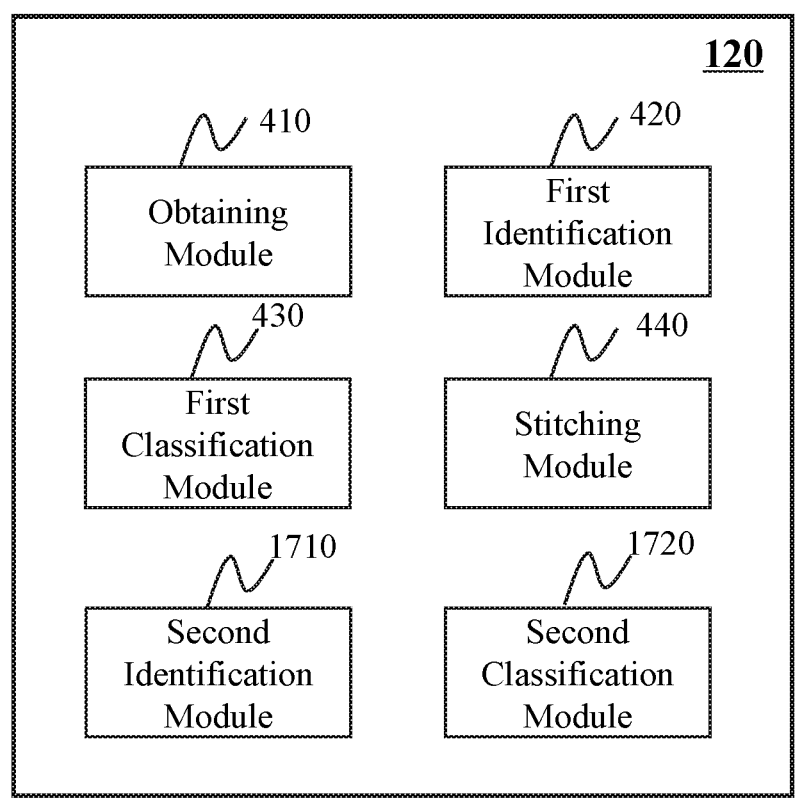
FIG. 17 is a block diagram illustrating an exemplary processing device according to some embodiments of the present disclosure.

FIG. 17 is a block diagram illustrating an exemplary processing device 120 according to some embodiments of the present disclosure. The processing device 120 may not only include components as illustrated in FIG. 4, such as the obtaining module 410, the first identification module 420, the first classification module 430 and the stitching module 440, but also a second identification module 1710 and a second classification module 1720. At least a portion of the processing device 120 may be implemented on the computing device as illustrated in FIG. 2 or the mobile device as illustrated in FIG. 3. The descriptions about the obtaining module 410, the first identification module 420, the first classification module 430 and the stitching module 440 may be found elsewhere in this disclosure (e.g., FIG. 4 and the descriptions thereof).

The second identification module 1710 may be configured to determine a sub-tag for the at least one of the one or more groups of image series. In some embodiments, the sub-tag may refer to a scan sequence of the image series of the same subject in the group of image series. For example, when a scanner (e.g., the scanner 110 as illustrated in FIG. 1) scans the same subject repeatedly, the corresponding scan sequence may be recorded. The second identification module 1710 may determine the sub-tag based on the recorded scan sequence.

The second classification module 1720 may be configured to classify the image series in one sub-group based on the sub-tags. In some embodiments, the second classification module 1720 may classify the image series having the same or substantially same sub-tag into the same group. As used herein, "substantially same" refers to that a similarity between each of the tags or sub-tags of the plurality of image series is larger than a threshold (e.g., 90%, 95%, 99%, etc.). In some embodiments, if the similarity is 100%, the "substantially same" means the "same" or "completely same". The second classification module 1720 may further determine one or more sub-groups based on the classification. In some embodiments, the second classification module 1720 may transmit the one or more sub-groups of image series to the stitching module 440 for further processing.

Figure 18:
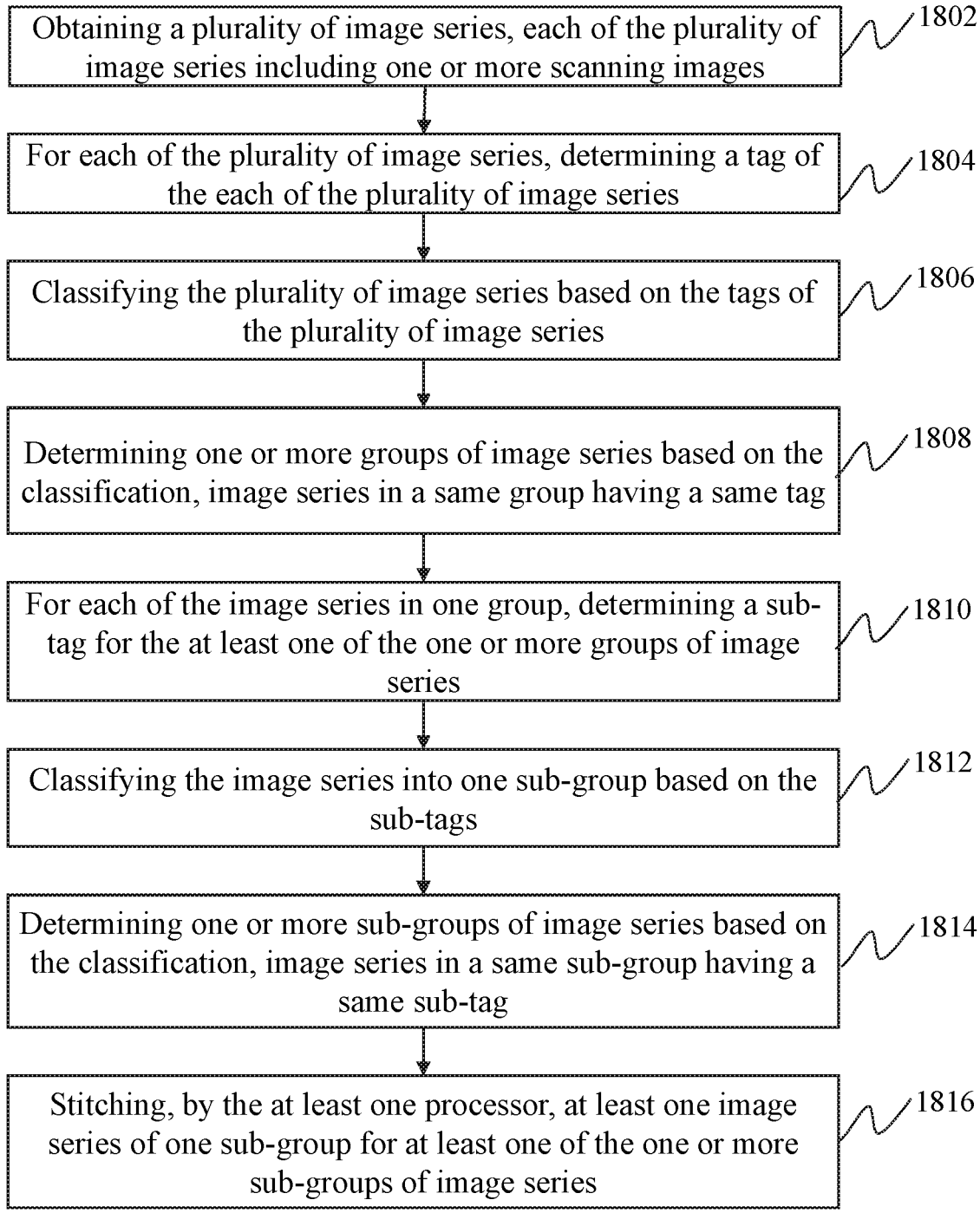
FIG. 18 is a flowchart illustrating an exemplary process for image processing according to some embodiments of the present disclosure.

FIG. 18 is flowchart illustrating an exemplary process 1800 for image processing according to some embodiments of the present disclosure. In some embodiments, one or more operations of process 1800 as illustrated in FIG. 18 for image processing, more particularly, image stitching, may be implemented in the imaging system 100 illustrated in FIG. 1. For example, the process 1800 may be stored in the storage device 130 in the form of instructions and be invoked and/or executed by the processing device 120 (e.g., the CPU 230 of the computing device 200 as illustrated in FIG. 2, the CPU 340 of the mobile device 300 as illustrated in FIG. 3). As another example, one or more operations of the process 1800 may be implemented on the scanner 110. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 18 and described below is not intended to be limiting.

The processing device 120 may produce an image series based on a scan and produce a plurality of image series based on multiple scans. In some embodiments, the quality of one or more scanning images included in an image series may not satisfy the requirements, such as image blurring, which may cause low accuracy of the corresponding stitching results of image series. Herein, the scanning image that could not satisfy the requirements may be designated as "unqualified image." The scanning image that could satisfy the requirements may be designated as "qualified image." In some embodiments, the user may customize the requirements of scanning images based on an image index. For example, the image index may include an image definition, an image contrast, an image sharpness, or the like, or any combination thereof. The subject may be scanned repeatedly in order to obtain qualified images. In the case, one or more image series relating to the same subject (e.g., a lung) may be obtained. In some embodiments, the one or more same image series relating to the same subject may be stitched according to the process 1800 as illustrated in FIG. 18.

Operations 1802-1810 may be similar to operations 502-510 of the process 500 and/or operations 702-716 of the process 700 described above, the detailed descriptions of which may be found in this disclosure in connection with FIGS. 5 and 7.

In 1810, for each of the image series in one group, the processing device 120 (e.g., the second identification module 1710 of the processing device 120) may determine a sub-tag for the at least one of the one or more groups of image series. In some embodiments, the sub-tag may refer to a scan sequence of the image series of the same subject in the group of image series. The scan sequence may be represented by j. In some embodiments, when a scanner (e.g., the scanner 110 as illustrated in FIG. 1) scans the same subject repeatedly, the corresponding scan sequence may be recorded. For example, when the scanner 110 scans a lung at the first time, j is equal to 1. Similarly, when the scanner 110 scans the lung at the second time, j is equal to 2. The processing device 120 may determine the sub-tag based on a value of j.

In 1812, the processing device 120 (e.g., the second classification module 1720 of the processing device 120) may classify the image series into one sub-group based on the sub-tags. For example, when the scanner 110 scans the subject at the first time, if all the image series of the subject are unqualified, the scanner 110 may scan the same subject at the second time. The processing device 120 may classify the image series having the sub-tag (j) of 2 into the same sub-group. Similarly, as illustrated in 1814, the processing device 120 may determine one or more sub-groups of image series based on the classification. The image series in the same sub-group may have the same or substantially same sub-tag. In some embodiments, it should be understood that operations 1810-1814 may be performed before stitching at least one image series of one sub-group.

In some embodiments, when the scanner (e.g., the scanner 110) scans the first subject at the first time, if all the image series of the first subject are qualified, the sub-tag of image series may be 1. When the scanner scans the second subject, the image series obtained by both the first scan and the second scan may be not qualified until the third scan, the sub-tag of image series obtained by the third scan may be 3. The processing device 120 may classify the image series having sub-tag of 1 and the image series having sub-tag of 3 into a sub-group.

In 1816, the processing device 120 (e.g., the stitching module 440 of the processing device 120) may stitch at least one image series of one sub-group for at least one of the one or more sub-groups of image series. In some embodiments, the processing device 120 may stitch all image series of one sub-group. For example, the user selects sub-group D of image series to stitch. The sub-group D may include one or more image series. A stitching algorithm may be selected according to the instructions form the user, such as the GA algorithm. The processing device 120 may stitch all image series of sub-group D based on the selected algorithm into a single image. In some embodiments, the processing device 120 may stitch a selected image series of the sub-group. For example, assuming that sub-group D may include three image series. The three image series may be represented by P1, P2, P3, respectively. Series P2 and P3 may be selected to stitch. Then the processing device 120 may just stitch series P2 and P3 into a single image based on the selected algorithm (e.g., GA algorithm). In some embodiments, the processing device 120 may stitch any combination of the image series of the sub-group. The image series may be combined based on a permutation method (e.g., $C_n^m$). For example, the sub-group D may include three image series. The three image series may be represented by P1, P2, P3, respectively. Obviously, there are three combinations for the image series of sub-group A (i.e., P1P2, P1P3, P2P3). The processing device 120 may stitch any one of the three combinations into a single image. It should be noted that, the processing device 120 may output the image series included in the sub-group without the stitching operation if a sub-group includes only one image series.

In some embodiments, before stitching the at least one image series of one sub-group, the processing device 120 may perform the data checking for the one or more sub-groups. The data checking is similar to the above description of the data checking as illustrated in FIG. 5, and not repeated herein.

It should be noted that the description of the process 1800 is provided for the purposes of illustration and not intended to limit the scope of the present disclosure. For persons having ordinary skills in the art, various variations and modifications may be conducted under the teaching of the present disclosure. However, those variations and modifications do not depart from the scope of the present disclosure. For example, operations 1812 and 1814 may be integrated into one single operation.

It should be noted that the above descriptions of the embodiments are provided for the purposes of comprehending the present disclosure, and not intended to limit the scope of the present disclosure. For persons having ordinary skills in the art, various variations and modifications may be conducted in the light of the present disclosure. However, those variations and the modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a frame wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB.NET, Python or the like, conventional procedural programming languages, such as the "C" programming language, Visual Basic, Fortran 2008, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution—e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. An image stitching method implemented on a machine having at least one processor and a storage device, the method comprising:
    obtaining, by at least one processor, a plurality of image series of multiple subjects acquired in multiple scans, each of the plurality of image series including one or more scanning images, and corresponding to one of the multiple scans in which one of the multiple subjects is scanned;
    for each of the plurality of image series, determining, by the at least one processor, a tag of the each of the plurality of image series;
    classifying, by the at least one processor, the plurality of image series based on the tags of the plurality of image series;
    determining one or more groups of image series based on the classification, image series in one of the one or more groups having a same tag;
    for each of the plurality of image series, determining a quality of the image series by checking the each image series based on a first factor and a second factor, the first factor relating to one or more scanning images of the each image series, and the second factor relating to scanning images of the each image series and of at least another image series of the plurality of image series; and
    for each group of at least one group of the one or more groups of image series,
        determining a sub-tag for each image series in the group, wherein the sub-tags relate to scan sequences of scans of a same subject of the multiple subjects corresponding to the image series in the group;
        determining, based on the sub-tags and corresponding qualities for stitching of the image series in the group, a sub-group of image series corresponding to the multiple subjects; and
        stitching, by the at least one processor, at least one image series of the sub-group.

2. The method of claim 1, further comprising:
    displaying, by a display, a plurality of stitching algorithms;
    receiving, by an input device, one or more instructions from a user; and determining, by the at least one processor, based on the one or more instructions, a selected stitching algorithm among the plurality of stitching algorithms, wherein stitching the at least one image series of the sub-group includes:
stitching, by the at least one processor, the at least one image series of the sub-group according to the selected stitching algorithm.

3. The method of claim 1, wherein stitching, by the at least one processor, the at least one image series of the sub-group includes stitching all image series of the sub-group.

4. The method of claim 1, wherein stitching, by the at least one processor, the at least one image series of the sub-group includes:
receiving, by an input device, a first selection instruction;
selecting, according to the first selection instruction, at least one image series of the sub-group; and
stitching, by the at least one processor, the selected at least one image series of the sub-group.

5. The method of claim 1, further comprising causing a stitching result to be displayed by a display.

6. The method of claim 1, wherein the tag includes at least one of a protocol title, a specific mark, or a name format of the plurality of image series.

7. An image stitching system, comprising:
at least one non-transitory computer-readable storage medium including a set of instructions;
at least one processor in communication with the at least one non-transitory computer-readable storage medium, wherein when executing the instructions, the at least one processor is configured to cause the system to:
obtain a plurality of image series of multiple subjects acquired in multiple scans, each of the plurality of image series including one or more scanning images and corresponding to one of the multiple scans in which one of the multiple subjects is scanned;
for each of the plurality of image series, determine a tag of the each of the plurality of image series;
classify the plurality of image series based on the tags of the plurality of image series;
determine one or more groups of image series based on the classification, image series in one of the one or more groups having a same tag;
for each of the plurality of image series, determining a quality of the image series by checking the each image series based on a first factor and a second factor, the first factor relating to one or more scanning images of the each image series, and the second factor relating to scanning images of the each image series and of at least another image series of the plurality of image series; and
for each group of at least one group of the one or more groups of image series,
determine a sub-tag for each image series in the group, wherein the sub-tags relate to scan sequences of scans of a same subject of the multiple subjects corresponding to the image series in the group;
determine, based on the sub-tags and corresponding qualities for stitching of the image series in the group, a sub-group of image series; and
stitch, by the at least one processor, at least one image series of the sub-group.

8. The system of claim 7, wherein the at least one processor is further configured to cause the system to:
display a plurality of stitching algorithms;
receive one or more instructions from a user; and
determine, based on the one or more instructions, a selected stitching algorithm among the plurality of stitching algorithms, wherein to stitch the at least one image series of the sub-group, the at least one processor is configured to cause the system to:
stitch the at least one image series of the sub-group according to the selected stitching algorithm.

9. The system of claim 8, wherein the at least one processor is further configured to cause the system to:
display a stitching result by a display.

10. The system of claim 8, wherein the tag includes at least one of a protocol title, a specific mark, or a name format of the plurality of image series.

11. The system of claim 10, wherein:
the multiple scans include one or more magnetic resonance scans, and
one or more of the tags of the plurality of image series relate to at least one of a longitudinal relaxation time, a transversal relaxation time, a fast spin echo sequence, or a gradient reunite echo sequence.

12. The system of claim 7, wherein to stitch the at least one image series of the sub-group, the at least one processor is configured to cause the system to:
stitch all image series of the sub-group.

13. The system of claim 7, wherein to stitch the at least one image series of the sub-group, the at least one processor is configured to cause the system to:
receive a first selection instruction;
select, according to the first selection instruction, at least one image series of the sub-group; and
stitch the selected at least one image series of the stitching combination sub-group.

14. The system of claim 7, wherein the image series in a same sub-group have a same sub-tag.

15. The system of claim 7, wherein to determine the quality of the image series by checking the each image series based on the first factor and the second factor, the at least one processor is further configured to cause the system to:
for the each image series, determine whether values of the first factor relating to at least two images in the image series are equal.

16. The system of claim 7, wherein the first factor includes at least one of a slice thickness, a slice gap, a pixel pitch, a field of view (FOV), a scanning direction, or a reference frame.

17. The system of claim 7, wherein to determine the quality of the image series by checking the each image series based on the first factor and the second factor, the at least one processor is further configured to cause the system to:
determine whether values of the second factor relating to at least two images from different image series of the at least one image series are equal.

18. The system of claim 7, wherein the second factor includes at least one of a slice thickness, a slice gap, a pixel pitch, reference coordinates, a view orientation, or a correction method.

19. A non-transitory computer-readable medium embodying a computer program product, the computer program product comprising instructions configured to cause a computing device to:
obtain a plurality of image series of multiple subjects acquired in multiple scans, each of the plurality of image series including one or more scanning images and corresponding to one of the multiple scans in which one of the multiple subjects is scanned;
for each of the plurality of image series, determine a tag of the each of the plurality of image series;

classify the plurality of image series based on the tags of the plurality of image series;
determine one or more groups of image series based on the classification, image series in one of the one or more groups having a same tag;
for each of the plurality of image series, determining a quality of the image series by checking the each image series based on a first factor and a second factor, the first factor relating to one or more scanning images of the each image series, and the second factor relating to scanning images of the each image series and of at least another image series of the plurality of image series; and
for each group of at least one group of the one or more groups of image series,
  determine a sub-tag for each image series in the group, wherein the sub-tags relate to scan sequences of scans of a same subject of the multiple subjects corresponding to the image series in the group;
  determine, based on the sub-tags and corresponding qualities for stitching of the image series in the group, a sub-group of image series; and
stitch, by the at least one processor, at least one image series of the sub-group.

* * * * *